United States Patent [19]
Cox et al.

[11] Patent Number: 5,393,732
[45] Date of Patent: Feb. 28, 1995

[54] TRIAZOLE PHOSPHORIC ACID DERIVATIVES AND THEIR USE AS HERBICIDES

[75] Inventors: John M. Cox, Wokingham; Peter Bellini, Purley on Thames; Roger Barrett, Stevenage; Russell M. Ellis, Bracknell; Timothy R. Hawkes, Priestwood, all of England

[73] Assignee: Zeneca Limited, London, England

[21] Appl. No.: 6,567

[22] Filed: Jan. 21, 1993

[30] Foreign Application Priority Data

Feb. 10, 1992 [GB] United Kingdom ............... 9202779

[51] Int. Cl.[6] ................... A01N 57/08; C07F 9/6518
[52] U.S. Cl. ................................ 504/197; 548/119
[58] Field of Search .............. 548/110, 119; 504/193, 504/197

[56] References Cited

U.S. PATENT DOCUMENTS 4,865,837  9/1989  Harris, III et al. ............ 424/10
5,248,655  9/1993  Hayakawa et al. ............ 548/119

FOREIGN PATENT DOCUMENTS 078613     5/1983   European Pat. Off. .
058760     2/1993   European Pat. Off. .
2016526    5/1970   France .
2428204    1/1975   Germany .
92/19629  11/1992   WIPO .

*Primary Examiner*—Patricia L. Morris
*Attorney, Agent, or Firm*—Marian T. Thomson

[57] ABSTRACT

A herbicidal compound of formula (I)

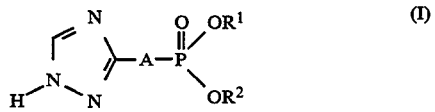

or a salt, tautomer or cyclic derivative thereof; where $R^1$ and $R^2$ are hydrogen and A is an optionally substituted saturated or unsaturated chain or ring of three carbon atoms.

Methods for preparing these compounds, intermediates used in the preparation and herbicidal compositions containing them are also described and claimed.

5 Claims, No Drawings

TRIAZOLE PHOSPHORIC ACID DERIVATIVES AND THEIR USE AS HERBICIDES

The present invention relates to novel phosphonic acid derivatives having herbicidal activity, to processes and intermediates used in their preparation and to herbicidal compositions containing them.

EP-A-0078613 describes certain triazole phosphonic acid derivatives and their use as herbicides. Copending International Patent Application No. WO92/19629 describes other such compounds.

According to the present invention there is provided a herbicidal compound of formula (I) or salts, tautomers or cyclic derivatives thereof: wherein $R^1$ and $R^2$ are hydrogen and A is an optionally substituted saturated or unsaturated chain or ring of 3 carbon atoms.

Suitable optional substituents for A include optionally substituted alkyl optionally substituted aryl, $OR^3$, $SR^4$, $S(O)_pR^a$, $NR^5R^6$, cycloalkyl, azido, heterocyclyl, optionally substituted oximino, oxo, optionally substituted hydrazono, nitrosyloxy, nitro, carboxy or salts or esters thereof, cyano or halogen: where $R^3$ is selected from hydrogen, optionally substituted acyl, optionally substituted aroyl, optionally substituted alkyl, optionally substituted aryl, amino, mono- or di-alkyl amino, $SO_2R^7$ or $SiR^bR^cR^d$ where $R^7$ is optionally substituted alkyl or optionally substituted aryl, and $R^b$, $R^c$ and $R^d$ are independently selected from alkyl or aryl; $R^4$ is selected from hydrogen, optionally substituted alkyl, optionally substituted aryl, optionally substituted acyl, optionally substituted aroyl, optionally substituted alkoxythiocarbonyl; $R^a$ is selected from optionally substituted alkyl or optionally substituted aryl and p is 1 or 2; $R^5$ is selected from hydrogen, optionally substituted alkyl, hydroxy, optionally substituted alkoxy, optionally substituted acyl, optionally substituted aroyl, $C(NR^e)R^fR^g$, $C(O)NR^fR^g$, $C(O)OR^f$ or $NR^fR^g$ where $R^e$, $R^f$ and $R^g$ are independently selected from hydrogen or alkyl; $R^6$ is hydrogen or optionally substituted alkyl; or two substituents may together with the carbon atoms to which they are attached form an epoxide or an optionally substituted aziridine ring.

As used herein the term "alkyl" includes chains having from 1 to 6, suitably from 1 to 3 carbon atoms. The term "cycloalkyl" refers 3 to 7 carbon atoms. The term "lower" refers to groups having up to 4 carbon atoms. The term "acyl" includes groups of formula $C(O)R^{15}$, where $R^{15}$ is alkyl, such as acetyl. The expression "optionally substituted acyl" refers to said groups wherein alkyl group $R^{15}$ carries optional substituents. The term "halogen" include fluorine, chlorine, bromine and iodine. The term "aryl" includes phenyl.

The term "heterocyclyl" refers to rings of up to 7 atoms, up to three of which are selected from oxygen, nitrogen and sulphur, such as 1,2,4-triazol-1-yl or pyridinium. The term "aroyl" includes benzoyl.

Unless otherwise stated, suitable optional substituents for all alkyl, acyl, alkoxy, alkoxythiocarbonyl groups mentioned herein include halogen, alkoxy, alkylthio, nitro, amino, carboxy or salts or esters thereof and aryl which in turn may be optionally substituted by alkyl, halo, alkoxy, alkylthio, haloalkyl, nitro, aryl, amino, carboxy or salts or esters thereof. Suitable optional substituents for oximino, hydrazono or aziridine groups include alkyl or alkyl substituted by aryl. An example of said optional substituents is benzyl.

Unless otherwise stated, suitable optional substituents for aryl or aroyl groups are alkyl, halogen, alkoxy, alkylthio, haloalkyl, nitro, amino, aryl and carboxy or salts or esters thereof.

Examples of A groups include groups of sub-formulae (i) to (vi).

In these groups $R^8$ is suitably selected from hydrogen, $OR^3$, $SR^4$, $S(O)_pR^a$, $NR^5R^6$, optionally substituted alkyl, optionally substituted aryl, azido, cycloalkyl, heterocyclyl, halogen, nitrosyloxy, nitro, cyano or carboxy or salts or esters thereof; where $R^3$, $R^4$, $R^5$, $R^6$, $R^a$ and p are as defined above.

$R^9$ is suitably hydrogen, halogen in particular fluorine, optionally substituted alkyl such as trifluoromethyl or optionally substituted aryl: or $R^9$ together with $R^8$ forms an oxo group, optionally substituted oximino group or optionally substituted hydrazono group.

$R^{10}$ is suitably selected from hydrogen, $OR^3$, $NR^5R^6$, $SR^4$, $S(O)_pR^a$, azido, optionally substituted alkyl, optionally substituted aryl, cycloalkyl, nitro, cyano, carboxy or salts or esters thereof or fluoro where $R^3$, $R^4$, $R^5$, $R^6$, $R^a$ and p are as hereinbefore defined except that $R^3$ is preferably other than $SO_2R^7$ where $R^7$ is as hereinbefore defined.

Alternatively $R^{10}$ together with $R^9$ constitute —O—, —NH—, —NCOR$^{14}$—, —NCO$_2$R$^{14}$— or —NSO$_2$R$^{14}$— where $R^{14}$ is alkyl or aryl.

The group $R^{10a}$ is suitably selected from hydrogen, fluoro, optionally substituted alkyl, optionally substituted aryl, amino, mono- or di-alkyl amino wherein any alkyl groups are optionally substituted as discussed above, azido, nitro, optionally substituted alkoxy or $OSiR^bR^cR^d$, where $R^b$, $R^c$ and $R^d$ are as defined above.

$R^{11}$ is suitably selected from hydrogen, optionally substituted alkyl, optionally substituted aryl or together with $R^{10}$ forms an oxo group, optionally substituted oximino or optionally substituted hydrazono group.

$R^{12}$ and $R^{13}$ are suitably independently selected from hydrogen, hydroxy or halogen in particular fluorine, provided that when one of $R^{12}$ or $R^{13}$ is hydroxy, the other is hydrogen.

Alternatively $R^{12}$ together with $R^9$ forms a bond.

As used herein the term "cyclic derivatives" refers to compounds derived from compounds of formula (I) where the group A is a saturated chain containing a leaving substituent at the 3-position. When the pH is raised so that the phosphonate group becomes dianionic, such compounds cyclise to form a compound of structure (IA) where $Z^+$ is an cation of valency n. n is suitably 1, 2 or 3. Suitable leaving substituents include halogen, $OSO_2R^7$ or nitrosyloxy.

Preferred examples of group A are those of sub-formulae (i) to (iii), most preferably those of sub-formulae (i).

Compounds of formula (I) can exist in diastereoisomeric forms, geometric isomeric forms and optically active forms. The present invention includes all such forms and mixtures thereof in all proportions.

When A is a group of sub formula (i), particular examples of $R^8$ are hydrogen, hydroxy, fluorine, chlorine, bromine, iodine, 1,2,4-triazol-1-yl, cyano, nitrosyloxy, aminoxy, acetoxy, haloacetoxy, methoxy, amino, azido, $SCSOCH_2CH_3$, $SCOCH_3$, mercapto, methylthio, methanesulphonyl or methanesulphinyl. A sub group of $R^8$ is fluorine, chlorine, bromine, iodine, 1,2,4-triazol-1-yl, cyano, nitrosyloxy, amino, aminoxy, haloacetoxy, methoxy, azido, $SCSOCH_2CH_3$, $SCOCH_3$, mercapto, methylthio, methanesulphonyl or methanesulphinyl.

Preferably $R^8$ is a leaving group such as nitrosyloxy or halo to enable the cyclic derivative to form, or amino.

Examples of $R^9$ are hydrogen, trifluoromethyl or fluorine, or $R^9$ together with $R^8$ forms an oxo or oximino group.

Particular examples of $R^9$ are hydrogen, fluorine, or $R^9$ together with $R^8$ forms a oximino group.

Particular examples of $R^{10}$ include hydrogen, hydroxy or amino.

Preferably $R^{11}$ is hydrogen.

Examples of $R^{12}$ and $R^{13}$ include hydrogen, hydroxy and fluorine, provided that when one of $R^{12}$ and $R^{13}$ is hydroxy, the other is hydrogen. Additionally $R^{12}$ together with $R^9$ forms a bond.

A sub group of compounds of formula (I) are as defined above provided that when A is a group of sub formula (i), and $R^{10}$, $R^{11}$, $R^{12}$ and $R^{13}$ are all hydrogen, either $R^8$ and $R^9$ do not together form a carbonyl group, or when $R^8$ is hydroxy or acetoxy, $R^9$ is other than hydrogen.

A further sub group of compounds of formula (I) comprise those where $R^1$ and $R^2$ are hydrogen, and A is a group of sub formula (ii), (iii), (iv) (v) or (vi).

A further sub group of compounds of formula (I) comprise those where $R^1$ and $R^2$ are hydrogen, A is a group of sub formula (i) in which $R^8$ is selected from $OR^{3''}$, $SR^4$, $S(O)_pR^a$, $NR^5R^6$, optionally substituted alkyl, optionally substituted aryl, azido, cycloalkyl, heterocyclyl, halogen, nitrosyloxy, nitro, cyano or carboxy or salts or esters thereof;

where $R^4$, $R^5$, $R^6$, $R^a$ and p are as defined above and $R^{3''}$ is selected from optionally substituted acyl other than unsubstituted acetyl, optionally substituted aroyl, optionally substituted aryl, substituted alkyl other than benzyl, amino mono- or di-alkyl amino or $SO_2R^7$ where $R^7$ is optionally substituted alkyl or optionally substituted aryl, $R^9$ is hydrogen, halogen, optionally substituted alkyl or optionally substituted aryl;

or $R^9$ together with $R^8$ forms an oximino groups or hydrazono group;

$R^{10}$ is suitably selected from hydrogen $OR^3$, $NR^5R^6$, $SR^4$, $S(O)_pR^a$, azido, optionally substituted alkyl, optionally substituted aryl, cycloalkyl, nitro, cyano, carboxy or salts or esters thereof or fluoro where $R^3$, $R^4$, $R^5$, $R^6$, $R^9$ and p are as hereinbefore defined except that $R^3$ is other than $SO_2R^7$;

or $R^{10}$ together with $R^9$ constitute —O—, —NH—, —NHCOR$^{14}$—, —NCO$_2$R$^{14}$— or —NSO$_2$R$^{14}$— where $R^{14}$ is alkyl or aryl; $R^{11}$ is selected from hydrogen, optionally substituted alkyl, optionally substituted aryl or together with $R^{10}$ forms an oxo or oximino group; and $R^{12}$ and $R^{13}$ are independently selected from hydrogen, hydroxy or halogen provided that when one of $R^{12}$ or $R^{13}$ is hydroxy, the other is hydrogen; or $R^{12}$ together with $R^9$ forms a bond.

According to another embodiment the present invention there is provided a herbicidal compound of formula (I) or salts or tautomers thereof: where $R^1$ and $R^2$ are hydrogen and A is an optionally substituted saturated or unsaturated chain of 3 carbon atoms.

Suitable optional substituents for A include one or more groups selected from alkyl, $OR^{3'}$, $SR^{4'}$, $NR^{5'}R^{6'}$, azido, cycloalkyl, oximino, oxo, or halogen, where $R^{3'}$ and $R^{4'}$ are independently selected from hydrogen, alkyl or aryl, and $R^{3'}$ may additionally be $SO_2R^{7'}$ where $R^{7'}$ is optionally substituted alkyl or aryl, and $R^{5'}$ and $R^{6'}$ are independently hydrogen, lower alkyl, hydroxy or acyl provided that when one of $R^{5'}$ and $R^{6'}$ is acyl, the other is hydrogen. Two substituents may together with the carbon atoms to which they are attached form an epoxide or aziridine ring. Suitable optional substituents for alkyl groups $R^{7'}$ include one or more halogens such as fluorine. Suitable optional substituents for aryl groups $R^{7'}$ include one or more substituents selected from alkyl, nitro, halogen.

Examples of A groups include groups of sub formulae (i) to (vi). In these groups $R^8$ is suitably hydrogen $OR^{3'}$, $SR^{4'}$, $NR^{5'}R^{6'}$, azido or halogen in particular fluorine, $R^9$ is suitably hydrogen, or $R^8$ and $R^9$ together form an oxo or oximino group.

$R^{10}$ is suitably hydrogen, hydroxy, $NH_2$, NHOH, SH or $OR^{3'}$ where $R^{3'}$ is alkyl or $R^{10}$ together with $R^8$ constitute —O—, —NH— or —NCO$_2$R$^{14'}$— where $R^{14'}$ is alkyl.

$R^{11}$ is suitably hydrogen or together with $R^{10}$ forms an oxo or oximino group.

$R^{12}$ and $R^{13}$ are suitably independently selected from hydrogen or halogen in particular fluorine.

A sub group of compounds of formula (I) are compounds where $R^1$ and $R^2$ are hydrogen, A is a group of sub-formulae (i), (ii), (iii), (iv), (v) or (vi) wherein $R^8$, $R^9$, $R^{10}$, $R^{11}$, $R^{12}$ and $R^{13}$ are independently selected from hydrogen, alkyl, $OR^{3'}$, $SR^{4'}$, $NR^{5'}R^{6'}$, azido, cycloalkyl, oximino, or halogen, where $R^{3'}$, $R^{4'}$, $R^{5'}$, $R^{6'}$ are as hereinbefore defined, or two of $R^8$, $R^9$, $R^{10}$, $R^{11}$, $R^{12}$ and $R^{13}$ together with the carbon atoms to which they are attached form a carbonyl group or an epoxide or aziridine ring, provided that when A is a group of sub-formula (i) and $R^{10}$, $R^{11}$, $R^{12}$ and $R^{13}$ are all hydrogen, $R^8$ and $R^9$ do not together with the carbon atom to which they are attached form an carbonyl group, or when one of $R^8$ or $R^9$ is hydrogen or $OR^{3'}$, and $R^{3'}$ is hydrogen, benzyl, acetyl or lower alkyl, the other is not hydrogen.

Suitable salts of formula (I) are agriculturally acceptable salts such as those formed with alkali metals, alkaline earth metals, ammonium, organic ammonium, trialkylsulphonium, trialkylsulphoxonium, phosphonium, and amidinium cations. The term organic ammonium cation is intended to include ammonium cations prepared from low molecular weight amines, that is to say those having a molecular weight below about 300. Examples of such amines include alkylamines, alkenylamines, and alkanolamines containing not more than two amino groups, such as methylamine, ethylamine, n-propylamine, isopropyl-amine, n-butylamine, isobutylamine, sec-butylamine, n-amylamine, isoamylamine, dimethylamine, diethylamine, di n-propylamine, diisopropylamine, trimethylamine, triethylamine, tri-n-propylamine, triisopropylamine, tri-n-butylamine, ethanolamine, n-propanolamine, isopropanolamine, diethanolamine, dipropanolamine, N,N-diethylethanolamine, allylamine, methoxyethylamine, oleylamine, cyclohexylamine, tallowamine, ethylenediamine, propylene-diamine, aniline, o, m and p-methoxy-substituted aniline, o, m and p-toluidine and heterocyclic amines, for example pyridine, morpholine, piperidine and pyrrolidine.

Tetra-substituted ammonium cations are also included, for example tetra-methylammonium, tetra-butylammonium, and benzyltrimethylammonium cations.

Trialkylsulphonium cations include those, for example, in which each of the three alkyl groups, which are not necessarily all the same, may contain from 1 to 6 carbon atoms. Trialkylsulphoxonium cations likewise include those in which each of the three alkyl groups, which may be the same or different, may contain from 1 to 6 carbon atoms.

Phosphonium cations include, for example, cations in which the phosphorus atom bears four substituents, each of which may be an alkyl group of one to ten carbon atoms or a phenyl group, for example the tetramethylphosphonium tetrabutylphosphonium, and tetraphenylphosphonium cations.

Amidinium cations include, for example, straight-chain amidinium cations of formula $R^hC(NH_2)NH_2^+$ wherein $R^h$ is an alkyl radical of, for example, from 1 to 10 carbon atoms, and cyclic amidinium cations such as the protonated form of 1,8-diazabicyclo[5,4,0]undec-7-ene (DBU). Alkali metal cations include lithium, sodium, and potassium; and alkaline earth metal cations include magnesium, calcium, strontium and barium.

Other salts are acid addition salts such as hydrochloride or hydrobromide salts.

When the group A includes a carboxy group, this may be in the form of salts or ester thereof. The salts are suitably agriculturally acceptable salts as outlined above. The esters are suitably agriculturally acceptable esters such as optionally substituted alkyl or optionally substituted aryl esters.

Examples of compounds of formula I are given in Table I hereinafter.

Compounds of formula (I) can be prepared by deesterifying and if necessary deprotecting a compound of formula (II); where A is as defined in relation to formula (I), B is a 1,2,4-triazol-3-yl group or a protected form thereof and $R^{20}$ and $R^{21}$ are independently selected from esterifying groups.

Protected triazolyl groups B are those of sub-formula (a) or (b), where $R^{22}$ is a protecting group such as triphenylmethyl (trityl), benzyl or 2-(trimethylsilyl)ethoxymethyl. A preferred protecting group is trityl.

As used herein, the expression "protecting group" refers to a group which can be introduced into an intermediate and the protected intermediate so-formed can withstand reaction conditions used to further react this intermediate, but which can, when desired, be removed under reaction conditions which do not disrupt the required final product.

Preferably the protecting group $R^{22}$ is removed in the same reaction step as the deesterifying process to remove $R^{20}$ and $R^{21}$ but if necessary or appropriate the deprotection reaction may be carried out separately.

Suitable esterifying groups $R^{20}$ and $R^{21}$ are alkyl; aryl; alkyl substituted by aryl; or trialkylsilyl. Specific examples of such groups are lower alkyl, phenyl, benzyl, or trimethylsilyl groups. In particular $R^{20}$ and $R^{21}$ are selected from isopropyl or ethyl.

Compounds of formula (II) are novel and as such form a further aspect of the invention.

Deesterification is suitably effected by reaction with a suitable reagent such as trimethylsilyl bromide, trimethylsilyl iodide, or trimethylsilyl chloride in the presence of iodide ion, or a strong acid such as hydrochloric acid.

Reaction temperatures and solvents will depend upon the particular reagent employed. For example, trimethylsilyl bromide and trimethylsilyl iodide can be used in dichloromethane at moderate temperatures, conveniently at ambient temperature. Trimethylsilyl chloride in the presence of iodide can be used in acetonitrile at moderate temperatures of from room temperature to reflux temperatures. When strong hydrochloric acid for example 6M-12M hydrochloric acid is employed, elevated temperatures up to the boiling point of the acid are suitable.

The applicants have found that compounds of formula (II) where B is a group of sub-formula (b) and $R^{22}$ is trityl can be converted to the equivalent compound where B is a group of sub-formula (a) by reaction with triphenylphosphine hydrobromide or trifluoroacetic acid or hydrogen chloride as exemplified hereinafter. The reaction is suitably effected at temperatures of from 0° C. to 100° C. in an inert solvent such as dichloromethane or chloroform.

Compounds of formula (II) can be prepared by reacting a compound of formula (III), where A' is a group A as hereinbefore defined or a group A where any substituent is protected, B is as defined in relation to formula (II) and X is a leaving group, with a compound of formula (IV), where $R^{20}$ and $R^{21}$ are as defined in relation to formula (II) and $R^{23}$ is hydrogen or alkoxy, preferably lower alkoxy such as ethyloxy or isopropoxy, or $R^{23}$ is a trialkylsilyloxy group such as trimethylsilyloxy.

Examples of leaving group X are halogen, in particular bromine or iodine, or sulphonates.

When $R^{23}$ is hydrogen, the reaction is suitably effected at temperatures of from −20° C. to 100° C., conveniently at ambient temperatures in an organic solvent such as N,N-dimethylformamide, toluene or tetrahydrofuran in the presence of a strong base such as sodium hydride. Where $R^{23}$ is other than hydrogen the compounds of formulae (III) and (IV) can be reacted directly together at temperatures of from 20° to 250° C., optionally in the presence of a solvent such as dichloromethane where appropriate. The reactions are usually effected under an inert atmosphere such as nitrogen.

Compounds of formula (III) are novel and these also form part of the invention.

They can be prepared by for example introducing a halogen atom or sulphonate group into a compound of formula (V), where A' and B are as hereinbefore defined. This can be effected by reacting a halogen in particular bromine, or a halogen-containing compound, such as carbon tetrabromide, in the presence of a trivalent phosphorus compound such as triphenyl phosphine, with the compound of formula (V) at temperatures of from −20° C. to 100° C., in an organic solvent such as dichloromethane or chloroform.

Other routes can be envisaged for specific compounds of formula (III). In one such case, a compound of formula (III), where B is as hereinbefore defined and A'—X is a group —CH=CH—CH$_2$Br, can be converted into the corresponding fluoride, for example by reaction with tetrabutylammonium fluoride. The fluoride is then halogenated with N-bromosuccinimide under free-radical conditions to prepare the compound of formula (III) where A'—X is —CH=CHCHFBr, as exemplified hereinafter.

Compounds of formula (V), where B is a protected triazole group are novel and form a further aspect of the invention. In particular the present invention provides compounds of formula (V) other than the compound where B is a group of sub-formula (b), $R^{22}$ is trityl and A'—OH is a 3-trialkylsilyloxypropanol. Compounds of formula (V) where A' is —CH=CHCH$_2$— can be prepared by reducing a compound of formula (VI), wherein B is as hereinbefore defined, or by reducing a compound of formula (V) where A' is —C≡C—CH$_2$—.

Compounds of formula (VI) are novel and form part of the invention. The reduction of compounds of formula (VI) is suitably effected using a reducing agent such as sodium borohydride in an inert solvent such as isopropanol or isopropanol mixed with chloroform. Reduction of the product, for example using hydrogen and a catalyst such as palladium/carbon, produces the equivalent compound of formula (V) where A' is —CH$_2$CH$_2$CH$_2$—. Reduction of a compound of formula (V) where A' is —C≡C—CH$_2$— can be complete, to give a compound where A' is —CH$_2$CH$_2$—CH$_2$—, or may be partial to give a compound of formula (V) where A' is —CH=CH—CH$_2$—.

Compounds of formula (VI) can be prepared by reaction of a compound of formula (VII), where B is as hereinbefore defined, with formylmethylenetriphenylphosphorane. The reaction is suitably effected at temperature of from 0° to 150° C., in an inert solvent such as dichloromethane, toluene, tetrahydrofuran or ethyl acetate. Similar reactions are envisaged where the triphenylphosphine moiety is replaced by a dialkyl or diphenyl phosphonate group. The Wittig or Wadsworth-Emomons reaction can also be carried out with the carbon residue in the phosphorus-containing reagent being at an oxidation level other than aldehyde and the product manipulated appropriately to give compounds of formula (VI). Alternatively reagents at the alcohol level give rise to products which can be converted to compounds of formula (V).

Compounds of formula (VII) where B is a group of sub-formula (b) can be prepared by reacting triazole with a halide of formula R$^{22}$-halide, for example triphenylmethyl chloride, and subsequently reacting the product with N,N-dimethylformamide in the presence of a strong base such as N-butyllithium and an additive such as N,N,N,N'-tetramethylethylenediamine. Suitable reaction conditions are exemplified hereinafter. In particular the present invention provides compounds of formula (VII) other than the compound where B is a group of sub-formula (b) and R$^{22}$ is trityl.

Compounds of formula (VII) where R$^{22}$ in group B is other than benzyl are novel and as such form part of the invention. In particular the present invention provides compounds of formula (VII) other than that where B is a group of sub formula (b) and R$^{22}$ is trityl.

Compounds of formula (V) where A' is —C≡C—CH$_2$— can be prepared by reacting a compound of formula (VIII), where B is as hereinbefore defined and R$^{25}$ is a leaving group, such as halide for example iodide or bromide, with for example propargyl alcohol in the presence of a palladium catalyst, such as tetrakis(triphenylphosphine)palladium. The reaction is effected in the presence of, for example, cuprous iodide and an amine base such as triethylamine. Suitable reaction conditions are described hereinafter.

Compounds of formula (VIII) are suitably prepared by halogenating the anion of a protected 1,2,4 triazole as exemplified hereinafter.

Compounds of formula (III), (V), (VI), (VII) and (VIII) where B is a group of sub formula (b) as defined hereinbefore can be converted to a corresponding compound where B is a group of sub-formula (a) as hereinbefore defined by reaction with triphenylphosphine hydrobromide or an acid such as trifluoroacetic acid or hydrogen chloride as described previously for a similar conversion in respect of compounds of formula (II).

Alternatively compounds of formula (II), (VII) and (VIII) where B is a group of sub formula (a) can be prepared by tritylating the appropriate 3-substituted 1,2,4-triazoles, with any substituents protected as necessary, as exemplified hereinafter.

Compounds of formula (II) where A is a group of sub-formula (v), R$^8$ is hydroxy and R$^9$ is hydrogen, can be prepared by reacting a compound of formula (VII) as hereinbefore defined with a compound of formula (IX), where R$^{20}$ and R$^{21}$ are as hereinbefore defined. The reaction is suitably effected at reduced temperatures of from −100° to 0° C., in the presence of a strong base such as n-butyllithium, under an inert atmosphere such as nitrogen, and in an inert organic solvent such as dry tetrahydrofuran. The product can be converted to other compounds of formula (II) where A is a group of sub-formula (i) or (ii) by hydrogenation. Conversion of the hydroxy group to other substituents, such as halogen, oxo, oximino or amino, can be carried out using conventional chemical manipulation techniques as exemplified hereinafter.

Alternatively compounds of formula (II) where A is a group of sub formula (i) and R$^8$ is hydroxy can be prepared by reacting the anion of a suitably-protected 1,2,4-triazole with an aldehyde of formula (X) where R$^{20}$ and R$^{21}$ are as hereinbefore defined. Temperatures of from −100° C. to −20° C. are suitably employed and the reaction is quenched at about −70° C. or less. Solvents such as tetrahydrofuran are employed. The anion is prepared as described before in relation to the preparation of compounds of formula (VII).

The compounds of formula (IX) are known but the applicants have found a better route for preparing them. According to one aspect of the invention there is provided a process for preparing a compound of formula (IX), as hereinbefore defined, which process comprises reacting a compound of formula (XII), where R$^{27}$ is a protecting group such as trimethylsilyl, with a compound of formula (XIII), where R$^{28}$ is a leaving group such as halogen and R$^{20}$ and R$^{21}$ are as hereinbefore defined, in the presence of a base such as n-butyllithium, oxidising the phosphonite product to the desired phosphonate, and deprotecting the compound of formula (XI) produced where R$^{20}$, R$^{21}$ and R$^{27}$ are as hereinbefore defined. The oxidation step may be carried out separately or in situ by adding an oxidising reagent, such as 3-chloroperbenzoic acid, to the reaction mixture. The deprotection is suitably effected using potassium fluoride as reagent in a solvent such as ethanol, or with aqueous sodium carbonate solution.

Compounds of formula (II) where A is —CH=C=CH— can be prepared by rearrangement of the corresponding compound of formula (II) where A is —C≡C—CH$_2$—, by reaction for example with basic alumina, or by reaction of a compound of formula (XIV), where B is as hereinbefore defined, with a compound of formula (XIII) as hereinbefore defined in the presence of a base. The reaction is preferably effected in the presence of a base such as 4-dimethylaminopyridine in an inert solvent such as dichloromethane.

Compounds of formula (XIV) are suitably prepared by reacting a compound of formula (VII) as hereinbefore defined with a compound of formula (XII), where R$^{27}$ is a protecting group such as trimethylsilyl, in the presence of a base, and subsequently removing the silicon protecting group. Suitable bases include strong bases such as n-butyl lithium. Deprotection is effected in a conventional manner, for example using potassium fluoride.

Compounds for example of formula (I) or (II) can be converted to other such compounds by manipulation of the group A to different such groups. In a further aspect of the invention there is provided a process for preparing a compound of formula (I) as defined in claim 1, which process comprises modifying a compound of formula (IIA); where B is as defined above, A' is a group A as defined above or a group A where any substituent is protected and $R^{20'}$ and $R^{21'}$ are $R^{20}$ and $R^{21}$ respectively as defined above or one or both are hydrogen; to change one group A' to another said group, and thereafter if necessary de-esterifying and/or deprotecting the product.

For example, where A is unsaturated, substituents can be added by standard addition techniques. These substituents may themselves be converted to different substituents or indeed removed again by methods which would be clear to the skilled chemist. Examples of such manipulations are provided hereinafter. Regio- and stereo-specific routes to compounds of formula (I) can be envisaged and these form part of the invention.

The compounds of formula (I) are active as herbicides and therefore, in a further aspect the invention provides a process for severely damaging or killing unwanted plants which process comprises applying to the plants, a herbicidally effective amount of a compound of formula (I) as hereinbefore defined.

The compounds of formula (I) are active against a broad range of weed species including monocotyledonous and dicotyledonous species. They show some selectivity towards certain species; they may be used for example as selective herbicides in soya, sugar beet and oil-seed rape crops.

The compounds of formula (I) may be applied directly to the plant (post-emergence application).

The compounds of formula (I) may be used on their own to inhibit the growth of, severely damage, or kill plants but are preferably used in the form of a composition comprising a compound of the invention in admixture with a carrier comprising a solid or liquid diluent.

Therefore, in yet a further aspect the invention provides plant growth inhibiting, plant damaging, or plant killing compositions comprising a compound of formula (I) as hereinbefore defined and an inert carrier or diluent.

Compositions containing compounds of formula (I) include both dilute compositions, which are ready for immediate use, and concentrated compositions, which require to be diluted before use, usually with water. Preferably the compositions contain from 0.01% to 90% by weight of the active ingredient. Dilute compositions ready for use preferably contain from 0.01% to 2% of active ingredient, while concentrated compositions may contain from 20% to 90% of active ingredient, although from 20% to 70% is usually preferred.

The solid compositions may be in the form of granules, or dusting powders wherein the active ingredient is mixed with a finely divided solid diluent, e.g. kaolin, bentonite, kieselguhr, dolomite, calcium carbonate, talc, powdered magnesia, Fuller's earth and gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution or dispersion of an active ingredient in water optionally containing a surface-active agent.

Surface-active agents may be of the cationic, anionic, or non-ionic type or mixtures thereof. The cationic agents are, for example, quaternary ammonium compounds (e.g. cetyltrimethylammonium bromide). Suitable anionic agents are soaps; salts of aliphatic mono ester of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate, and a mixture of the sodium salts of diisopropyl and triisopropylnaphthalenesulphonic acid. Suitable non-ionic agents are the condensation products of ethylene oxide with fatty alcohols such as oleyl alcohol and cetyl alcohol, or with alkylphenols such as octyl- or nonyl-phenol (e.g. Agral 90) or octylcresol. Other non-ionic agents are the partial esters derived from long chain fatty acids and hexitol anhydrides, for example sorbitan monolaurate; the condensation products of the partial ester with ethylene oxide; the lecithins; and silicone surface active agents (water soluble surface active agents having a skeleton which comprises a siloxane chain e.g. Silwet L77). A suitable mixture in mineral oil is Atplus 411F.

The aqueous solutions or dispersions may be prepared by dissolving the active ingredient in water or an organic solvent optionally containing wetting or dispersing agent(s) and then, when organic solvents are used, adding the mixture so obtained to water optionally containing wetting or dispersing agent(s). Suitable organic solvents include, for example, ethylene di-chloride, isopropyl alcohol, propylene glycol, diacetone alcohol, toluene, kerosene, methylnaphthalene, the xylenes and trichloroethylene.

The compositions for use in the form of aqueous solutions or dispersions are generally supplied in the form of a concentrate containing a high proportion of the active ingredient, and the concentrate is then diluted with water before use. The concentrates are usually required to withstand storage for prolonged periods and after such storage, to be capable of dilution with water to form aqueous preparations which remain homogeneous for a sufficient time to enable them to be applied by conventional spray equipment. Concentrates conveniently contain 20–90%, preferably 20–70%, by weight of the active ingredient(s). Dilute preparations ready for use may contain varying amounts of the active ingredient(s) depending upon the intended purpose; amounts of 0.01% to 10.0% and preferably 0.1% to 2%, by weight of active ingredient(s) are normally used.

A preferred form of concentrated composition comprising the active ingredient which has been finely divided and which has been dispersed in water in the presence of a surface-active agent and a suspending agent. Suitable suspending agents are hydrophilic colloids and include, for example, polyvinylpyrrolidone and sodium carboxymethylcellulose, and the vegetable gums, for example gum acacia and gum tragacanth. Preferred suspending agents are those which impart thixotropic properties to, and increase the viscosity of the concentrate. Examples of preferred suspending agents include hydrated colloidal mineral silicates, such as montmorillonite, beidellite, nontronite, hectorite, saponite, and saucorite. Bentonite is especially preferred. Other suspending agents include cellulose derivatives and polyvinyl alcohol.

The compositions of the invention may comprise, in addition to one or more compounds of the invention, one or more compounds not of the invention but which possess biological activity for example herbicides, fungicides, insecticides (optionally with an insecticide synergist) and plant growth regulators. Accordingly in yet a still further embodiment the invention provides a herbicidal composition comprising a mixture of at least one herbicidal compound of formula (I) as hereinbefore defined with at least one other herbicide.

The other herbicide may be any herbicide not having the formula (I). It will generally be a herbicide having a complementary action in the particular application.

Examples of useful complementary herbicides include:

A. benzo-2,1,3-thiadiazin-4-one-2,2-dioxides such as bentazone;
B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, clopyralid, and their derivatives (e.g. salts, esters and amides);
C. 1,3 dimethylpyrazole derivatives such as pyrazoxyfen, pyrazolate and benzofenap;
D. Dinitrophenols and their derivatives (eg. acetates) such as dinoterb, dinoseb and its ester, dinoseb acetate;
E. dinitroaniline herbicides such as dinitramine, trifluralin, ethalflurolin, pendimethalin, oryzalin;
F. arylurea herbicides such as diuron, flumeturon, metoxuron, neburon, isoproturon, chlorotoluron, chloroxuron, linuron, monolinuron, chlorobromuron, daimuron, methabenzthiazuron;
G. phenylcarbamoyloxyphenylcarbamates such as phenmedipham and desmedipham;
H. 2-phenylpyridazin-3-ones such as chloridazon and norflurazon;
I. uracil herbicides such as lenacil, bromacil and terbacil;
J. triazine herbicides such as atrazine, simazine, aziprotryne, cyanazine, prometryn, dimethametryn, simetryne, and terbutryn;
K. phosphorothioate herbicides such as piperophos, bensulide, and butamifos;
L. thiolcarbamate herbicides such as cycloate, vernolate, molinate, thiobencarb, burylate*, EPTC*, triallate, di-allate, esprocarb, tiocarbazil, pyridate, and dimepiperate;

\* These compounds are preferably employed in combination with a safener such as dichlormid.

M. 1,2,4-triazin-5-one herbicides such as metamitron and metribuzin;
N. benzoic acid herbicides such as 2,3,6-TBA, dicamba and chloramben;
O. anilide herbicides such as pretilachlor, butachlor, alachlor, propachlor, propanil, metazachlor, metolachlor, acetochlor, and dimethachlor;
P. dihalobenzonitrile herbicides such as dichlobenil, bromoxynil and ioxynil;
Q. haloalkanoic herbicides such as dalapon, TCA and salts thereof;
R. diphenylether herbicides such as lactofen, fluroglycofen or salts or ester thereof, nitrofen, bifenox, aciflurofen and salts and esters thereof, oxyfluorfen, fomesafen, chlornitrofen and chlomethoxyfen;
S. phenoxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;
T. cyclohexanedione herbicides such as alloxydim and salts thereof, sethoxydim, cycloxyidim, tralkoxydim, and clethodim;
U. sulfonyl urea herbicides such as chlorosulfuron, sulfometuron, metsulfuron and esters thereof; benzsulfuron and esters thereof such as DPX-M6313, chlorimuron and esters such as the ethyl ester thereof pirimisulfuron and esters such as the methyl ester thereof, 2-[3-(4-methoxy-6-methyl-1,3,5-triazin-zyl)-3-methylureidosulphonyl] benzoic acid esters such as the methyl ester thereof (DPX-LS300) and pyrazosulfuron;
V. imidazolidinone herbicides such as imazaquin, imazamethabenz, imazapyr and isopropylammonium salts thereof, imazethapyr;
W. arylanilide herbicides such as flamprop and esters thereof, benzoylprop-ethyl, diflufenican;
X. amino acid herbicides such as glyphosate and glufosinate and their salts and esters, sulphosate and bialaphos;
Y. organoarsenical herbicides such as monosodium methanearsonate (MSMA);
Z. herbicidal amide derivative such as napropamide, propyzamide, carbetamide, tebutam, bromobutide, isoxaben, naproanilide and naptalam;
AA. miscellaneous herbicides including ethofumesate, cinmethylin, difenzoquat and salts thereof such as the methyl sulphate salt, clomazone, oxadiazon, bromofenoxim, barban, tridiphane, flurochloridone, quinclorac, dithiopyr and mefanacet;
BB. Examples of useful contact herbicides include: bipyridylium herbicides such as those in which the active entity is paraquat and those in which the active entity is diquat;

The following examples illustrate the invention. In the Examples the group triphenylmethyl has been referred to as 'trityl' throughout and as CPh₃ in the formulae drawings. Where phosphonic acids are eluted from Amberlite CG-120(H+) non-exchange resin with aqueous ammonium hydroxide, the amount of ammonium ion present in the final product is variable depending not only upon the structure of the acid itself and the amount of ammonia in the particular eluant fraction but also upon the exact conditions under which water is removed. In the following Examples, no mention is made of ammonium salt formation in the final product.

EXAMPLE 1

This Example illustrates the preparation of 1-trityl-1,2,4-triazole. A solution of trityl chloride (417.7 g) in dichloromethane (1.21) was added slowly over two hours, whilst maintaining the temperature below 50° C. by external cooling, to a solution of 1,2,4-triazole (103.5 g) and triethylamine (151.5 g, 209 ml) in N,N-dimethylformamide (500 ml). The mixture was then stirred for a further one hour, poured into water (21) and extracted with dichloromethane (5×500 ml). The extracts were dried over magnesium sulphate, evaporated under reduced pressure and the crude product triturated with ether (200 ml total) to give the title compound (425 g, m.p. 213°–214° C.). NMR (CDCl₃): $\delta$7.1–7.4 (15H,m), 8.03(1H,s), 8.08(1H,s).

EXAMPLE 2

This Example illustrates the preparation of 1-trityl-1,2,4-triazole-5-carboxaldehyde. A solution of 1-trityl- 1,2,4-triazole (62.2 g, prepared as described in Example 1) and N,N,N',N'-tetramethylethylenediamine (23.2 g, 30 ml) in dry tetrahydrofuran (1 l) was cooled to −70° C. under nitrogen. n-Butyllithium (140 ml, 1.6M solution in hexane) was added dropwise, with stirring, at such a rate that the internal temperature was maintained below −60° C. The dark red solution was stirred at −70° C. for at least thirty minutes, treated dropwise with N,N-dimethylformamide (25 ml), allowed to warm to −30° C., then quenched with water (500 ml). The mixture was extracted with ethyl acetate (500 ml), containing a little dichloromethane if any solid precipitated. The extracts were washed with water (6×500 ml), dried over magnesium sulphate, evaporated under reduced pressure and the crude product triturated with ether-hexane (1:1, 150 ml) to give the title compound (60 g, m.p. 134°–136° C.). This can be contaminated with 1,2,4-triazole itself, but subsequent stages are not adversely affected and the impurity can be removed at a later stage. NMR (CDCl$_3$): δ7.1–7.4 (15H,m), 8.1(1H,s), 9.15(1H,s).

EXAMPLE 3

This Example illustrates the preparation of 1-trityl-1,2,4-triazole-3-carboxaldehyde. Trifluoroacetic acid (0.5 ml) was added dropwise to a solution of 1-trityl-1,2,4-triazole-5-carboxaldehyde (5.0 g, prepared as described in Example 2) in dry dichloromethane (30 ml). A bright yellow colouration developed, then faded rapidly. The mixture was allowed to stand overnight at room temperature, diluted with dichloromethane, washed with sodium bicarbonate solution then brine, dried over magnesium sulphate and evaporated under reduced pressure to give the title compound (4.32 g). This was chromatographed on silica, using dichloromethane-ether (25:1) as eluant, to give material m.p. 181°–183° C. NMR (CDCl$_3$): δ7.1–7.4(15H,m), 8.13(1H,s), 10.05(1H,s). Other acids (e.g. a trace of hydrogen chloride gas) in solvents such as dichloromethane can also be used.

Alternative methods of preparing the title compound are as follows:

a) A solution of trityl chloride (43.4 g) in dichloromethane (120 ml) was added dropwise, over thirty minutes, to a stirred solution of 1,2,4-triazole-3-carboxaldehyde diethyl acetal (21.67 g, prepared as described by Mukahami et al, Heterocycles, 1981, 15, 301) and triethylamine (25 ml) in dichloromethane (200 ml). After stirring for a further three hours, the mixture was washed with water, dried over magnesium sulphate and evaporated under reduced pressure. A solution of the residual oil in ether (250 ml) crystallised to give 1-trityl-1,2,4-triazole-3-carboxaldehyde diethyl acetal (22.14 g, m.p. 120°–124° C.). Trimethylsilyl bromide (14 ml) was added rapidly to a stirred solution of this acetal (6.2 g) in toluene (80 ml). After a further fifteen minutes, the solution was poured into a rapidly-stirred mixture of saturated sodium carbonate solution (200 ml), solid sodium carbonate (10 g) and ethyl acetate (150 ml). The mixture was stirred rapidly for ten minutes, the phases separated and the organic layer washed with water, dried over magnesium sulphate, and evaporated under reduced pressure. The residual oil was chromatographed on silica, using dichloromethane-ether (25:1) as eluant, to give the title compound (2.57 g). The deacetalation can also be carried out using pyridinium p-toluenesulphonate in acetone.

b) Trityl chloride (19.0 g) was added portionwise to a stirred solution of 3-methyl-1,2,4-triazole (5.6 g, commercial) and triethylamine (9.5 ml) in dichloromethane (200 ml). The mixture was diluted with dichloromethane (100 ml), washed with water (50 ml), dried over magnesium sulphate and evaporated under reduced pressure to give 1-trityl-3-methyl-1,2,4-triazole (19.0 g). Recrystallisation of a 2 g sample from toluene-hexane (1:1) gave pure material (1.32 g, m.p. 194°–196° C.). NMR (CDCl$_3$): δ2.41(3H,s), 7.03–7.40(15H,m), 7.83(1H,s).

A solution of this material (5.6 g), N-bromosuccinimide (3.1 g) and α,α'-azoisobutyronitrile (50 mg) in carbon tetrachloride (150 ml) was heated under reflux, and illuminated with a 500 W halogen lamp, for two and a half hours. The mixture was cooled, diluted with dichloromethane (50 ml), washed with water (100 ml) and dried over magnesium sulphate. The extracts were evaporated under reduced pressure and the residual oil chromatographed on silica, using dichloromethane as eluant, to give 1-trityl-3-bromomethyl-1,2,4-triazole (2.8 g) as a pale yellow oil. NMR (CDCl$_3$): δ4.48(2H,s), 7.1–7.5(15H,m), 8.04(1H,s).

A solution of this material (2.8 g) and sodium bicarbonate (6.0 g) in dimethylsulphoxide (40 ml) was heated at 150° C. for fifteen minutes, cooled, and partitioned between water (150 ml) and dichloromethane (150 ml). The organic layer was washed with water (2×75 ml), dried over magnesium sulphate and evaporated under reduced pressure. The residual oil was chromatographed on silica, using dichloromethane-ether (25:1) as eluant, to give the title compound (1.3 g).

c) n-Butyllithium (18 ml, 1.6M in hexane) was added portionwise, under nitrogen, to a solution of 1,2,4-triazole (2.0 g) in dry tetrahydrofuran (200 ml). The mixture was stirred at room temperature for thirty minutes, treated with a solution of t-butyldimethylsilyl chloride (4.4 g) in tetrahydrofuran (10 ml), stirred for thirty minutes more, then cooled to −65° C. n-Butyllithium (18 ml, 1.6M in hexane) was added dropwise whilst maintaining the temperature below −65° C. The solution was stirred for a further thirty minutes at −60° C., treated with N,N-dimethylformamide (4.0 ml), then allowed to warm to room temperature over ninety minutes. It was diluted with water (20 ml) and ethanol (50 ml) and evaporated under reduced pressure. The residue was azeotroped with ethanol (2×100 ml), dissolved in N,N-dimethylformamide (50 ml), and treated with triethylamine (4.0 ml), then portionwise with trityl chloride (8.0 g). The solution was stirred for thirty minutes, diluted with dichloromethane (200 ml), washed with water (3×100 ml), dried over magnesium sulphate and evaporated under reduced pressure. The residual oil was chromatographed on silica, using dichloromethane-ether (25:1) as eluant, to give the title compound (5.15 g).

EXAMPLE 4

This Example illustrates the preparation of 1-trityl-5-iodo-1,2,4-triazole.

A stirred solution of 1-trityl-1,2,4-triazole (9.95 g, prepared as described in Example 1) and N,N,N',N'-tetramethylethylenediamine (3.71 g) in dry tetrahydrofuran (200 ml) was cooled to −70° C. under nitrogen and treated dropwise with n-butyllithium (22.0 ml, 1.6M solution in hexane). The solution was stirred for ten minutes, then treated rapidly with a solution of iodine (10.0 g) in dry tetrahydrofuran (40 ml). After a further one minute, the mixture was quenched at −50° C. with 0.1M sodium thiosulphate (100 ml) and portioned between dichloromethane and water. The organic layer was washed with water, dried over magnesium sulphate, evaporated under reduced pressure and the residue chromatographed on silica, using dichloromethane-ether (25:2) as eluant to give the title compound (11.73 g, m.p. 248°–250° C.). NMR (CDCl$_3$): δ7.1–7.3 (15H,m), 8.0(1H,s). $^{13}$C NMR confirmed position of substitution. M/S: M+ 437

EXAMPLE 5

This Example illustrates the preparation of 1-trityl-3-iodo-1,2,4-triazole.

A solution of 1-trityl-5-iodo-1,2,4-triazole (5.5 g, prepared as described in Example 4) and triphenylphosphine hydrobromide (0.1 g) in dichloromethane (60 ml) was stirred for five minutes, diluted with dichloromethane and washed with 0.1M sodium thiosulphate solution (100 ml). The organic layer was dried over magnesium sulphate, evaporated under reduced pressure and the residue chromatographed, using dichloromethane-ether (25:2) as eluant, to give the title compound (5.37 g, m.p. 245°–246° C.). NMR (CDCl$_3$): δ7.1–7.3(15H,m), 7.8(1H,s). $^{13}$C NMR confirmed position of substitution. CI M/S: MH+, 438.

EXAMPLE 6

This Example illustrates the preparation of 1-trityl-3-bromo-1,2,4-triazole.

A stirred solution of 1-trityl-1,2,4-triazole (15.55 g, prepared as described in Example 1) and N,N,N',N'-tetramethylethylenediamine (5.8 g) in dry tetrahydrofuran (500 ml) was cooled to −70° C. under nitrogen and treated dropwise with n-butyllithium (37.5 ml, 1.6M in hexane). The deep-red solution was stirred at −70° C. for twenty minutes, then treated dropwise with a solution of bromine (10.4 g) in dry tetrahydrofuran (10 ml). The now brownish-yellow solution was allowed to warm to −20° C., quenched with 0.1M sodium thiosulphate solution (150 ml), and extracted with dichloromethane (500 ml). The organic layer was washed with water (4×100 ml), dried and evaporated. The residue was chromatographed on silica, using dichloromethane-ether (25:2) as eluant, to give 1-trityl-5-bromo-1,2,4-triazole (7.86 g, m.p. 239°–241° C.). NMR (CDCl$_3$):δ7.1–7.3(15H,m), 7.95(1H,s).

A solution of this material (0.78 g) and triphenylphosphine hydrobromide (0.05 g) in dry dichloromethane (10 ml) was allowed to stand for fifteen minutes, under nitrogen, then evaporated under reduced pressure. The residue was chromatographed on silica, using dichloromethane-ether (25:2) as eluant, to give the title compound (0.67 g, m.p. 230°–232° C.). NMR (CDCl$_3$): δ7.1–7.4(15H,m), 7.85(1H,s).

EXAMPLE 7

This Example illustrates the preparation of E-3(1-trityl-1,2,4-triazole-5-yl)propenal.

A solution of 1-trityl-1,2,4-triazole-5-carboxaldehyde (53.8 g, prepared as described in Example 2) in dry dichloromethane (300 ml) was heated to reflux under nitrogen, then treated dropwise with a solution of formylmethylenetriphenylphosphorane (48.3 g) in dichloromethane (200 ml) over a period of one hour. Heating was continued until no starting material remained, approximately three hours. The solvent was removed under reduced pressure and the residue chromatographed on silica gel, using dichloromethane-ether (25:2) as eluant, to give the title compound as a pale yellow solid (55.8 g, m.p. 197°–200° C.). NMR (CDCl$_3$):δ6.35(1H,d), 6.85(1H,dd), 7.05–7.4(15H,m), 8.05(1H,s), 9.05(1H,d). J$_{CH=CH}$ 15 Hz. A small quantity (1.4 g, m.p. 186°–188° C.) of the less polar Z-isomer was isolated from the chromatography. NMR(CDCl$_3$): δ5.69(1H,dd), 6.4(1H,d), 7.1–7.4(15H,m), 8.0(1H,s), 10.5(1H,d). J$_{CH=CH}$ 10 Hz.

EXAMPLE 8

This Example illustrates the preparation of E-3(1-trityl-1,2,4-triazol-3-yl)propenal.

A mixture of 1-trityl-1,2,4-triazole-3-carboxaldehyde (5.28 g, prepared as described in Example 3), formylmethylenephosphorane (4.26 g) and dry toluene (150 ml) was heated under reflux, under nitrogen for three hours. The mixture was cooled, evaporated under reduced pressure and chromatographed on silica, using dichloromethane-ether (25:1) as eluant, to give the title compound (3.0 g, m.p. 162°–164° C.). NMR (CDCl$_3$): δ7.0–7.4(15H+1H,m), 7.5(1H,d), 8.03 (1H,s), 9.73(1H,d). J$_{CH=CH}$ 16 Hz M/S: M+ 365. This material can also be obtained by rearrangement of the 5-yl isomer, prepared as described in Example 7, using triphenylphosphine hydrobromide in chloroform.

EXAMPLE 9

This Example illustrates the preparation of E-3(1-trityl-1,2,4-triazol-5-yl)prop-2-en-1-ol.

A stirred solution of 3(1-trityl-1,2,4-triazol-5-yl)propenal (91.25 g, prepared as described in Example 7) in chloroform (800 ml) was diluted with isopropanol (800 ml), then treated portionwise with sodium borohydride (9.50 g) over a period of forty-five minutes. An exotherm to 30°–35° C. can occur. The mixture was stirred until no starting material remained, about one hour more, then quenched by addition of saturated ammonium chloride solution over a period of several hours. It was then filtered through Hyflo Super-Cel, evaporated under reduced pressure and the residue dissolved in a mixture of chloroform (500 ml, ethyl acetate (500 ml) and water (200 ml). The organic phase was washed with water (2×200 ml) and brine (200 ml), dried over magnesium sulphate and evaporated to give, after trituration with hexane, the product (90.0 g) as a white solid. Chromatography on silica, using ethyl acetate as eluant, followed by trituration with ether, gave material m.p. 150°–153° C. NMR (CDCl$_3$): δ1.65(1H,br), 3.9(2H,m), 5.65(1H,d), 6.7(1H,dt), 7.0–7.4(15H,m), 7.88(1H,s). J$_{CH=CH}$ 16 Hz. $^{13}$C NMR confirmed the position of substitution.

EXAMPLE 10

This Example illustrates the preparation of E-3(1-trityl-1,2,4-triazol-3-yl)prop-2-en-1-ol.

Sodium borohydride (0.13 g) was added to a stirred mixture of E-3(1-trityl-1,2,4-triazol-3-yl)propenal (1.26 g, prepared as described in Example 8) in isopropanol-chloroform (1:1, 40 ml). After a further fifteen minutes, the mixture was quenched with saturated ammonium chloride solution (5 ml), evaporated under reduced pressure and the residue extracted with a mixture of ethyl acetate and chloroform. The extract was dried and evaporated to give the title compound (1.25 g, m.p. 156°–160° C.). NMR (CDCl$_3$): δ4.33(2H,m), 6.7(1H,d), 6.87(1H,dt), 7.1–7.4(15H,m), 7.88(1H,s). $^{13}$C NMR confirmed the position of substitution.

EXAMPLE 11

This Example illustrates the preparation of E-1-bromo-3(1-trityl-1,2,4-triazol-5-yl)prop-2-ene.

A stirred solution of E-3(1-trityl-1,2,4-triazol-5-yl)prop-2-en-1-ol (9.36 g prepared as described in Example 9) and triphenylphosphine (13.38 g) in chloroform (125 ml) was heated dropwise, at −5° C. under nitrogen, with a solution of carbon tetrabromide (8.46 g) in chloroform (50 ml). The mixture was stirred for a further two hours at 0° C., evaporated under reduced pressure and chromatographed on silica, using dichloromethane-ether (25:2) as eluant, to give the title compound (6.42 g, m.p. 138° C. dec.). NMR (CDCl$_3$): δ3.65(2H,d), 5.6(1H,d), 6.7(1H,dt), 7.1–7.3(15H,m), 7.9(1H,s). M/S: M+ 430. $^{13}$C NMR confirms the position of substitution. Isomerisation to the 3-yl isomer can occur even on standing in chloroform but is preparatively best carried out by stirring with triphenylphosphine hydrobromide in chloroform.

The 5-yl isomer can also be made by an alternative procedure. Thus a stirred solution of triphenylphosphine (1.97 g) in tetrahydrofuran (30 ml) was treated, at 0° C., with diethyl azodicarboxylate (1.28 g). After twenty minutes, lithium bromide (1.3 g) was added, followed immediately by the 5-yl alcohol (1.09 g). After twenty minutes, the solvent was removed under reduced pressure and the residue chromatographed, as described above, to give the title compound (0.71 g).

EXAMPLE 12

This Example illustrates the preparation of E-1-bromo-3(1-trityl-1,2,4-triazol-3-yl)prop-2-ene.

A solution of bromine (16.0 g) in dichloromethane (100 ml) was added dropwise, at such a rate that the temperature was maintained below 0° C., to a stirred and cooled (initially −10° C.) solution of triphenylphosphine (26.2 g) in dichloromethane (250 ml). The white suspension was stirred for a further ten minutes, then treated dropwise with a solution of E-3(1-trityl-1,2,4-triazol-5-yl)prop-2-en-1-ol (36.7 g, prepared as described in Example 9) and triethylamine (10.1 g) in dichloromethane (100 ml), maintaining the temperature below 5° C. The solution was then stirred at room temperature until the rearrangement of the trityl group was complete (if necessary additional triphenylphosphine hydrobromide can be added). The solvent was removed under reduced pressure and the residue chromatographed on silica, using dichloromethane-ether (25:2) as eluant, to give the title compound (34.47 g, m.p. 168°–171° C. dec). NMR (CDCl$_3$): δ4.0(2H,d), 6.6(1H,d), 6.8(1H,dt), 7.1–7.4(15H,m), 7.9(1H,s). $^{13}$C NMR confirmed the position of substitution.

This reaction can also be carried out using carbon tetrabromide in place of bromine. The alternative approach of converting the 3-yl alcohol, prepared as described in Example 10, directly into the title compound is also possible.

EXAMPLE 13

This Example illustrates the preparation of 3(1,2,4-triazol-3-yl) propane phosphonic acid, (Compound No. 1 in Table 1).

A stirred solution of E-3(1-trityl-1,2,4-triazol-5-yl)prop-2-en-1-ol (9.5 g, prepared as described in Example 9) in dichloromethane (100 ml) was hydrogenated over 5% palladium-carbon (50 mg) at room temperature and pressure for four hours. The mixture was filtered through Hyflo Super-Cel, evaporated under reduced pressure and chromatographed, using ethyl acetate-hexane (4:1), then ethyl acetate, as eluants, to give 3(1-trityl-1,2,4-triazol-5-yl)propanol (7.1 g, m.p. 150°–152° C.). NMR (CDCl$_3$): δ1.4(2H,m), 2.2(2H,t), 3.45(2H,t), 7.1–7.3(15H,m), 7.9(1H,s).

A solution of bromine (5.6 g) in dichloromethane (15 ml) was added dropwise to a stirred solution of triphenylphosphine (9.2 g) in dichloromethane (100 ml) cooled to −5° C. The mixture was stirred for a further ten minutes at 0° C., then treated portionwise with a solution of the above alcohol (6.9 g) and triethylamine (4.9 ml) in dichloromethane (30 ml) again maintaining the temperature below 0° C. The solution was stirred for a further ten minutes, filtered through a bed of silica, then chromatographed on silica, using dichloromethane-ether (25:1) as eluant, to give 1-bromo-3(1-trityl-1,2,4-triazol-5-yl)propane (3.5 g, m.p. 146°–149° C.). NMR (CDCl$_3$): δ1.8(2H,m), 2.15(2H,t), 3.2(2H,t), 7.1–7.3(15H,m), 7.9(1H,s). $^{13}$C NMR was used to confirm the position of the trityl substituent.

Diethyl phosphite (1.2 ml) was added to a suspension of sodium hydride (0.4 g, 60% dispersion in mineral oil) in dry N,N-dimethylformamide (30 ml). The mixture was stirred for thirty minutes, then treated with a solution of the above bromide (2.0 g) in N,N-dimethylformamide (10 ml). After ninety minutes, the mixture was partitioned between ethyl acetate (150 ml) and 1M citric acid solution (100 ml). The organic layer was washed with water, dried over magnesium sulphate and evaporated under reduced pressure. The residue was chromatographed on silica, using dichloromethane-ethanol (20:1) as eluant, to give diethyl 3(1-trityl-1,2,4-triazol-5-yl)propane phosphonate (1.1 g, m.p. 141°–144° C.). NMR (CDCl$_3$): δ1.28(6H,t), 1.3–1.65(4H,m), 2.1(2H,t), 4.0 (4H,m), 7.1–7.3(15H,m), 7.9(1H,s). $^{13}$C NMR was used to confirm the position of the trityl substitutuent.

A solution of this phosphonate (0.5 g) and trimethylsilyl bromide (3 ml) in dry dichloromethane (30 ml) was allowed to stand overnight at room temperature, evaporated under reduced pressure, then azeotroped under reduced pressure with methanol (3×10 ml). The residue was partitioned between water (15 ml) and ether (30 ml). The aqueous layer was evaporated under reduced pressure and chromatographed on Amberlite CG-120(H+) resin, using first water, then 0.2M ammonium hydroxide solution, as eluant. Appropriate fractions were evaporated under reduced pressure, then freeze-dried, to give the title compound (0.13 g) as a gum. NMR (D$_2$O): δ 1.45(2H,m), 1.85(2H,m), 2.8(2H,t), 8.1(1H,s).

EXAMPLE 14

This Example illustrates the preparation of diisopropyl E-3(1-trityl-1,2,4-triazol-5-yl)prop-2-ene phosphonate having the structural formula (XV).

A mixture of E-1-bromo-3(1-trityl-1,2,4-triazol-5-yl)prop-2-ene (5.3 g, prepared as described in Example 11) and triisopropylphosphite (40 ml) was heated under nitrogen for ninety minutes at 180°–190° C., cooled and evaporated under reduced pressure. The residue was chromatographed on silica, using dichloromethane-ethanol (20:1) as eluant, to give, after trituration with ether, the title compound. (2.36 g, m.p. 157°–158° C.). NMR (CDCl$_3$): δ1.2(12H,2xd), 2.3(2H,2xd), 4.6(2H,m), 5.5(1H,dd), 6.6(1H,m), 7.1–7.3(15H,m), 7.9(1H,s). $^{13}$C NMR was used to confirm the position of trityl substitution.

EXAMPLE 15

This Example illustrates the preparation of diisopropyl E-3(1-trityl-1,2,4-triazol-3-yl)prop-2-ene phosphonate having the structural formula (XVI)

A mixture of E-1-bromo-3(1-trityl-1,2,4-triazol-3-yl)prop-2-ene (25.8 g, prepared as described in Example 12) and triisopropylphosphite (15.6 g) was heated under a gentle stream of nitrogen. When the internal temperature had reached 180° C., after thirty minutes, the reaction mixture was cooled and the product isolated by chromatography on silica, using ethyl acetate as eluant. Recrystallisation from ethyl acetate-hexane gave the title compound (19.16 g, m.p. 121°–123° C.). NMR (CDCl$_3$): $\delta$1.3(12H,m), 2.74(2H,dd), 4.72(2H,m), 6.55(1H,dd), 6.65(1H,m), 7.1–7.3(15H,m), 7.85(1H,s). J$_{CH=CH}$ 15 Hz.

This material can also be prepared by treating the corresponding 5-yl phosphonate (prepared as described in Example 14) with triphenylphosphine hydrobromide in chloroform for twelve hours at room temperature.

EXAMPLE 16

This Example illustrates the preparation of diethyl Z-3(1-trityl-1,2,4-triazol-3-yl)prop-2-ene phosphonate having the structural formula (XXIII).

Diethyl 3(1-trityl-1,2,4-triazol-3-yl)prop-2-yne phosphonate (0.84 g, prepared as described in Example 17) was hydrogenated over Lindlar catalyst (5% palladium on calcium carbonate poisoned with lead, initially 0.19 g). The reaction was extremely slow and was carried out over twenty seven-hour sessions adding fresh catalyst (0.10 g) every four periods. The reaction mixture was finally filtered through Hyflo Super-cel and evaporated under reduced pressure to give material having a ratio of alkene:alkyne of 8:1. Chromatography on silica, using ethyl acetate as eluant, gave the title compound (0.64 g) as a viscous oil. NMR (CDCl$_3$): $\delta$1.14(6H,t), 3.40(2H,dd), 3.92(4H,q), 5.87(1H,m), 6.49(1H,dd), 7.0–7.3(15H,m), 7.86(1H,s). J$_{CH=CH}$ 11 Hz.

EXAMPLE 17

This Example illustrates the preparation of diethyl 3(1-trityl-1,2,4-triazol-3-yl)prop-2-yne phosphonate having the structural formula (XVII).

A stirred solution of 1-trityl-3-iodo-1,2,4-triazole (26.24 g, prepared as described in Example 5), propargyl alcohol (3.56 ml) and triethylamine (40 ml) in dry N,N-dimethylformamide (750 ml) was treated successively with tetrakis(triphenylphosphine)palladium (2.77 g) and cuprous iodide (1.0 g). It was stirred for four hours at room temperature under nitrogen and allowed to stand overnight but the reaction had not proceeded to completion. Stirring was continued for a further four periods of seven hours, then the mixture was poured into water (1l) and extracted with chloroform (5×250 ml). The extracts were dried over magnesium sulphate, evaporated under reduced pressure and chromatographed on silica, using ethyl acetate-hexane (4:1) as eluant. Trituration with ether gave 1-hydroxy-3(1-trityl-1,2,4-triazol-3-yl)prop-2-yne (12.20 g). Recrystallisation from chloroform gave material m.p. 211° C. NMR (CDCl$_3$): $\delta$ 4.45(2H,s), 7.1–7.3(15H,m), 7.95(1H,s). $^{13}$C NMR provided confirmation. M/S: M+ 365.

A solution of bromine (1.72 ml) in dry dichloromethane (10 ml) was added dropwise to a stirred, cooled (−5° C.), solution of triphenylphosphine (8.74 g) in dry dichloromethane (140 ml) whilst maintaining the temperature below 0° C. The solution was stirred for a further ten minutes at 0° C., then treated dropwise over one hour with a solution of the above alcohol (12.17 g) and triethylamine (4.64 ml) in dry dichloromethane (200 ml). After ten minutes, the mixture was evaporated under reduced pressure and the residue chromatographed on silica, using dichloromethane-ether (25:2) as eluant, to give 1-bromo-3(1-trityl-1,2,4-triazol-3-yl)prop-2-yne (8.10 g, m.p. 181°–183° C. dec). NMR (CDCl$_3$): $\delta$4.1(2H,s), 7.05–7.35(15H,m), 7.95(1H,s). M/S: M+ 427,429.

A solution of sodium iodide (4.75 g) in acetone (100 ml) was added to a stirred solution of the above bromide (11.3 g) in acetone (900 ml). After six hours, the mixture was filtered and the filtrate evaporated under reduced pressure. The residue was triturated with ethyl acetate-hexane (1:1) to give 1-iodo-3(1-trityl-1,2,4-triazol-3-yl)prop-2-yne (9.68 g). Chromatography on silica, using ethyl acetate as eluant, gave material m.p. 176° C. dec. NMR (CDCl$_3$): $\delta$3.85(2H,s), 7.1–7.3(15H,m), 7.95(1H,s). M/S: M+ 475.

A solution of the above iodide (10.92 g) and diethyltrimethylsilyl phosphite (5.80 g) in dry dichloromethane (100 ml) was heated under reflux, under nitrogen, for two days, then allowed to stand at room temperature for three more days. It was evaporated under reduced pressure and the residue chromatographed on silica, using ethyl acetate as eluant, to give the title compound (4.10 g, m.p. 159°–161° C.). NMR (CDCl$_3$): $\delta$1.35(6H,dt), 3.0(2H,d), 4.22(4H,m), 7.1–7.35(15H,m), 7.95(1H,s). J$_{P-H}$ 22 Hz. M/S: M+ 485.

EXAMPLE 18

This Example illustrates the preparation of E-3(1,2,4-triazol-3-yl)-prop-2-ene phosphonic acid (Compound No. 2 in Table 1).

A stirred solution of diisopropyl E-3(1-trityl-1,2,4-triazol-3-yl)-prop-2-ene phosphonate (2.06 g, prepared as described in Example 15) in dry dichloromethane (30 ml) was treated with trimethylsilyl bromide (5.2 ml). The mixture was allowed to stand for three days, evaporated under reduced pressure and the residue azeotroped under reduced pressure with methanol (2×50 ml). The residue was then partitioned between water (40 ml) and ethyl acetate (40 ml). The aqueous layer was washed with ethyl acetate (40 ml) and evaporated under reduced pressure finally by freeze-drying. The residue was chromatographed on Amberlite CG-120(H+) resin, using water as an eluant. The appropriate fractions were evaporated, finally by freeze-drying, to give the title compound (0.52 g, m.p. 208°–210° C. dec). NMR (D$_2$O): $\delta$2.80(2H,dd), 6.60(1H,dd), 6.9(1H,m), 8.75(1H,s), J$_{CH=CH}$ 16 Hz. FAB M/S: M+ 189.

EXAMPLE 19

This Example illustrates the preparation of diisopropyl E-1-fluoro-3-(1-trityl-1,2,4-triazol-3-yl)prop-2-ene phosphonate having the structural formula (XVIII).

A stirred solution of E-1-bromo-3(1-trityl-1,2,4-triazol-3-yl)prop-2-ene) (34.47 g, prepared as described in Example 12) in dry dichloromethane (150 ml) was treated, under nitrogen, with tetrabutylammonium fluoride (160 ml, 1M in tetrahydrofuran). The mixture was heated under reflux for thirty minutes, cooled, washed with water (3×100 ml), dried over magnesium sulphate and evaporated under reduced pressure. The residue was chromatographed on silica, using dichloromethane-ether (25:2) as eluant, to give E-1-fluoro-3(1-trityl-1,2,4- triazol-3-yl)prop-2-ene (19.37 g, m.p. 149° C.). NMR (CDCl$_3$): δ4.95, 5.15(2H,dd), 6.7–6.9(2H,m), 7.1–7.3(15H,m), 7.9(1H,s). $J_{CH=CH}$ 16.1 Hz, $J_{HF}$ 46.8 Hz. $^{19}$F NMR (CDCl$_3$): −216.4 ppm vs. CFCl$_3$.

A stirred mixture of this material (11.07 g), N-bromosuccinimide (4.92 g) and α,α'-azoisobutyronitrile (200 mg) and carbon tetrachloride (100 ml) was heated under reflux, under nitrogen, for three hours. It was then filtered, evaporated under reduced pressure and chromatographed, using dichloromethane-ether (25:2) as eluant, to give E-1-bromo-1-fluoro-3-(1-trityl-1,2,4-triazol-3-yl)prop-2-ene (6.53 g, m.p. 145°–146° C.). NMR (CDCl$_3$): δ6.8–7.05(3H,m), 7.1–7.4(15H,m), 7.95(1H,s). NMR(C$_6$D$_6$): δ 6.05(1H,dd), 6.35(1H,dd), 6.65–6.85(15H,m), 7.0(1H,m), 7.55(1H,s). $J_{CH=CH}$ 15 Hz, $J_{HF}$ 50 Hz.

The structure was confirmed by $^{19}$F NMR (−134.6 ppm vs CFCl$_3$) and $^{13}$C NMR.

A mixture of this material (2.63 g) and triisopropylphosphite (2.2 ml) was heated under nitrogen until the internal temperature reached 185° C. The dark solution was allowed to cool, then heated at 60° C./0.05 mm in a Kugelrohr. The residue was chromatographed on silica, using ethyl acetate-ethanol (100:1) as eluant, to give the title compound (1.5 g) as a gum. NMR (CDCl$_3$): δ1.3(12H,m), 4.8(2H,m), 5.25,5.4(2H,m), 6.8(1H,m), 7.1–7.3(15H,m), 7.9(1H,s).

EXAMPLE 20

This Example illustrates the preparation of E-1-fluoro-3(1,2,4-triazol-3-yl)prop-2-ene phosphonic acid (Compound No. 3 in Table 1).

A mixture of diisopropyl E-1-fluoro-3(1-trityl-1,2,4-triazol-3-yl)-prop-2-ene phosphonate (0.26 g, prepared as described in Example 19), trimethylsilyl bromide (2.5 ml) and dichloromethane (10 ml) was allowed to stand for eighteen hours at room temperature, evaporated under reduced pressure, then azeotroped under reduced pressure with methanol (3×10 ml). The residue was partitioned between water (10 ml) and ether (10 ml) and the aqueous layer chromatographed on Amberlite CG-120 (H+) resin, using water as eluant. Appropriate fractions were freeze-dried to give the title compound (0.050 g, m.p.>150° C. dec). NMR (D$_2$O): δ5.35,5.5(1H,2xm), 6.7(1H,m), 7.0(1H,m), 8.9(1H,s). $J_{CH=CH}$ 15 Hz. FAB M/S: M+ 207.

EXAMPLE 21

This Example illustrates the preparation of 1-fluoro-3(1,2,4-triazol-3-yl)propane phosphonic acid (Compound No. 21 in Table I).

Diisopropyl E-1-fluoro-3(1-trityl-1,2,4-triazol-3-yl)prop-2-ene phosphonate (0.62 g, prepared as described in Example 19), was hydrogenated in dry isopropanol (10 ml) over 10% palladium on carbon (0.20 g) over a period of five days. The solution was filtered through Hyflo Super-Cel and evaporated under reduced pressure. The residue was chromatographed on silica, using ethyl acetate then ethyl acetate-ethanol (9:1) as eluant, to give diisopropyl 1-fluoro-3(1-trityl-1,2,4-triazol-3-yl)propane phosphonate (0.24 g) as a colourless gum. NMR (CDCl$_3$): δ1.3(12H,m), 2.3(2H,m), 3.0(2H,m), 4.7(2H,m and 1H,m), 7.05–7.4(15H,m), 7.85(1H,s). The structure was confirmed by $^{13}$C and $^{31}$P NMR. M/S: MH+ 536. Other fractions gave detritylated material (0.18 g), also as a clear gum.

A solution of the tritylated ester (0.22 g) and trimethylsilyl bromide (2.0 ml) in dry dichloromethane (10 ml) was allowed to stand for twenty hours, then treated as described for the unsaturated analogue in Example 20 to give the title compound (0.034 g, m.p. 146° C., dec). NMR (D$_2$O): δ2.1(2H,m), 3.0(2H,m), 4.35 and 4.6(1H,m), 8.7(1H,s). M/S: MH+ 210.

EXAMPLE 22

This Example illustrates the preparation of (1RS, 2RS, 3SR; 1SR, 2RS, 3SR)-1-fluoro-2,3-dihydroxy-3(1,2,4-triazol-3-yl)propane phosphonic acid (Compound No. 22 in Table I).

A mixture of diisopropyl E-1-fluoro-3(1-trityl-1,2,4-triazol-3-yl)-prop-2-ene phosphonate (0.11 g, prepared as described in Example 19), N-methylmorpholine N-oxide (0.047 g) and osmium tetroxide (0.05 ml, 2.5% in t-butanol) in t-butanol-tetrahydrofuran-water (10:3:1, 35 ml) was stirred at room temperature, under nitrogen, for four hours. The slow reaction was carried out over four days, adding fresh osmium tetroxide solution (0.1 ml) each day. Sodium dithionite (1.0 g) and water (10 ml) was added, the mixture stirred for thirty minutes and concentrated under reduced pressure. The residue was treated with brine (10 ml), made weakly acidic with 2M hydrochloric acid, then extracted with ethyl acetate. The extracts were washed with brine, dried over magnesium sulphate, filtered through Hyflo Supercel and evaporated under reduced pressure. This residue was purified by HPLC on silica, using dichloromethane-ethanol (15:1) as eluant, to give a single diastereomer (0.048 g) of protected title compound as a white solid. Another fraction (0.006 g) contained this material together with the other isomer.

The major component can be deesterified and detritylated in the usual way to give a single diastereoisomer of the title compound.

EXAMPLE 23

This Example illustrates the preparation of diethyl ethynylphosphonate having the structural formula (XIX).

The following is a considerable improvement on literature routes utilising dihaloacetylenes.

n-Butyllithium (26.02 ml, 1.55M in hexane) was added dropwise over thirty minutes to a stirred solution of trimethylsilylacetylene (5.18 ml) in dry tetrahydrofuran (25 ml), whilst maintaining the temperature below −65° C. After twenty minutes, diethylchlorophosphite (4.71 ml) was added dropwise over twenty minutes, then stirring continued for a further ninety minutes at −65° C. The stirred mixture was allowed to warm to −20° C., quenched by dropwise addition of saturated ammonium chloride solution (10 ml), then allowed to reach room temperature, diluted with water (10 ml) and extracted with chloroform (4×25 ml). The extracts were dried over magnesium sulphate and evaporated under reduced pressure to give diethyl trimethylsilylethynylphosphonite as a brown oil (7.34 g, 83% pure by GC).

A stirred solution of this material (6.6 g) in dichloromethane (150 ml) was treated portionwise with 3-chloroperbenzoic acid (6.21 g). After a further three hours, it was extracted with sodium carbonate solution (10%, 50 ml total) then water, dried over magnesium sulphate, and evaporated under reduced pressure. The crude diethyl trimethylsilylethynylphosphonate was dissolved in ethanol (100 ml) and treated with potassium fluoride (3.5 g). After two hours, water (100 ml) was added and the mixture extracted with chloroform (3×100 ml). The extracts were dried over magnesium sulphate, evaporated under reduced pressure and the residual oil (4.8 g) distilled in a Kugelrohr to give the title compound (4.0 g, b.p. 100°–110° C. (oven)/0.01 mm), 100% pure by GC. The desilylation step can also be carried out using aqueous sodium carbonate solution. Purification can also be carried out on silica, using ether as eluant. NMR (CDCl$_3$): δ1.36(6H,t), 2.96(1H,d), 4.16(4H,m). IR: 2065 cm$^{-1}$.

EXAMPLE 24

This Example illustrates the preparation of 3-hydroxy-3(1,2,4-triazol-3-yl)propane phosphonic acid (Compound No. 4 in Table 1).

n-Butyllithium (30 ml, 1.6M in hexane) was added dropwise to a stirred solution of diethyl ethynylphosphonate (6.32 g, prepared as described in Example 23) in dry tetrahydrofuran (50 ml), under nitrogen, whilst maintaining the temperature below −65° C. After stirring for a further two minutes, the solution was treated, dropwise below −65° C. with a solution of 1-trityl-1,2,4-triazole-3-carboxaldehyde (16.49 g, prepared as described in Example 3) in dry tetrahydrofuran (100 ml). The mixture was stirred for two hours at −70° C., allowed to warm to −40° C. over thirty minutes, then quenched into saturated ammonium chloride solution (100 ml) and ethyl acetate (200 ml). The extracts were dried over magnesium sulphate, evaporated under reduced pressure and the residual oil (23.69 g) chromatographed on silica, using dichloromethane-ethyl acetate (4:1), then dichloromethane-ethanol (19:1) as solvent, to give diethyl 3-hydroxy-3(1-trityl-1,2,4-triazol-3-yl)prop-2-yne phosphonate (9.52 g, m.p. 156°–158° C.). NMR (CDCl$_3$): δ1.25(6H,m), 4.1(4H,m), 4.65(1H,br), 5.7(1H,dd), 7.1–7.3(15H,m), 8.0(1H,s).

A solution of the above acetylene (6.41 g) in isopropanol (100 ml) was hydrogenated over platinum oxide (50 mg), at atmospheric pressure and room temperature, until hydrogen uptake ceased after five hours. The mixture was filtered through Hyflo Super-Cel the solution evaporated under reduced pressure, and the residue chromatographed on silica, using dichloromethane-ethanol (19:1) to give diethyl 3-hydroxy-3(1-trityl-1,2,4-triazol-3-yl)propane phosphonate (3.88 g, m.p. 119°–121° C.). NMR (CDCl$_3$): δ1.3(6H,t), 1.88–2.28(4H,m), 3.7(1H,d), 4.05(4H,m), 4.9(1H,q), 7.1–7.38(15H,m), 7.95(1H,s).

A solution of the ester (0.74 g) in dichloromethane (15 ml) was treated with trimethylsilyl bromide (4 ml) and allowed to stand overnight. It was then evaporated and the residue azeotroped under reduced pressure with methanol (3×20 ml), then partitioned between water (30 ml) and ether (60 ml). The aqueous layer was evaporated under reduced pressure and the residue chromatographed on Amberlite CG-120(H+) resin, using water as an eluant. Appropriate fractions were freeze-dried to give the title compound (0.17 g, m.p. 107°–109° C.). NMR (D$_2$O): δ1.4–1.6 (2H,m), 1.8–2.1(2H,m), 4.9(1H,q), 8.6(1H,s). The $^{13}$C NMR confirmed the structure. FAB M/S: MH+ 208.

The sequence can also be carried out using the corresponding 5-carboxaldehyde; here it is critical that quenching of the first stage reaction is carried out at <−40° C.

Alternative methods of preparing the title compound are as follows:

a) A solution of 1-trityl-1,2,4-triazole (10.0 g, prepared as described in Example 1) and N,N,N′,N′-tetramethylethylenediamine (3.8 g) in dry tetrahydrofuran (250 ml) was cooled to −70° C. under nitrogen. n-Butyllithium (22.2 ml, 1.6M solution in hexane) was added dropwise, with stirring, at such a rate that the internal temperature was maintained below −60° C. The red solution was stirred at −70° C. for twenty-five minutes, then treated dropwise with diethyl 3-oxo-propane phosphonate (6.20 g, prepared by formic acid deacetalisation of the diethyl acetal, DE 2517448, and also described in, for example, Tetrahedron 1981, 37, 1377) whilst maintaining the temperature at that level. The mixture was stirred for two and a half hours at −70° C. then quenched, at that temperature, with saturated aqueous ammonium chloride solution. It was extracted with ethyl acetate and the organic phase washed with brine, dried over magnesium sulphate, and evaporated under reduced pressure to give crude diethyl 3-hydroxy-3(1-trityl-1,2,4-triazol-5-yl)propane phosphonate (10.81 g). Chromatography on silica, using dichloromethane-ethanol (19:1) as eluant, gave pure material, m.p. 154°–155° C. NMR (CDCl$_3$): δ1.3(6H,t), 1.9(2H,m), 1.7(2H,m), 3.1(1H,br), 4.0(4H,m), 4.1(1H,t), 7.1–7.3 (15H,m), 7.9(1H,s). M/S: M+ 505.

A solution of crude material (10.81 g) in dry dichloromethane (100 ml) was treated with trifluoroacetic acid (3.0 ml), allowed to stand at room temperature for eighteen hours, diluted with dichloromethane, washed with saturated aqueous sodium bicarbonate solution, then brine, dried over magnesium sulphate and evaporated under reduced pressure. The residue (10.81 g) was chromatographed on silica, using dichloromethane-ethanol (19:1) as eluant, to give diethyl 3-hydroxy-3(1-trityl-1,2,4-triazol-3-yl)propane phosphonate (6.89 g, m.p. 119°–121° C.), having an NMR spectrum identical to that of material prepared by the alternative method described above. Silicon mediated deprotection gave the title compound.

b) Reaction of the triazolyl-aldehydes with the complex β-metallated ethylphosphonates reported in Tetrahedron Letters, 1990, 31, 1833 can also yield appropriate alcohols directly.

EXAMPLE 25

This Example illustrates the preparation of 3-methoxy-3(1,2,4-triazol-3-yl)propane phosphonic acid (Compound No 23 in Table I).

A stirred solution of diethyl 3-hydroxy-3(1-trityl-1,2,4-triazol-3-yl) propane phosphonate (1.0 g, prepared as described in Example 24) and 15-Crown-5 (0.02 g) in dry N,N-dimethylformamide (10 ml) was treated portionwise with sodium hydride (0.10 g, 60% in oil) whilst maintaining the temperature below 5° C. The cooled reaction mixture was stirred for twenty-five minutes, then treated with a solution of methyl iodide (0.70 g) in dry N,N-dimethylformamide (1.0 ml). It was allowed to warm to room temperature, to stand for eighteen hours, poured into water and extracted with ethyl acetate. The extracts were washed with water and brine, dried over magnesium sulphate, and evaporated under reduced pressure. The residue was chromatographed on silica, using dichloromethane-ethanol (49:1) as eluant, to give diethyl 3-methoxy-3(1-trityl-1,2,4-triazol-3-yl) propane phosphonate (0.46 g, m.p. 104° C.). NMR (CDCl$_3$): δ1.3(6H,m), 1.7–2.0(2H,m), 2.1–2.3(2H,m), 3.3(3H,s), 4.1(4H,m), 4.4(1H,t), 7.15(6H,m), 7.3(9H,m), 7.95(1H,s). M/S: M+ 519.

A solution of this material (0.65 g) and trimethylsilyl bromide (4.0 ml) in dichloromethane (15 ml) was allowed to stand for two days, then evaporated under reduced pressure. The residue was azeotroped with methanol (3×10 ml) under reduced pressure, then partitioned between water and ether. The aqueous phase was concentrated under reduced pressure, chromatographed on Amberlite CG-120(H+) resin and freeze-dried to give the title compound (0.11 g, m.p. 102°–103° C.). NMR (D$_2$O): δ1.4–1.7(2H,m), 2.0–2.2(2H,m), 3.25(3H,s), 4.6(1H,t), 8.7(1H,s). FAB M/S: MH+ 222.

EXAMPLE 26

This Example illustrates the preparation of 3-acetoxy-3(1,2,4-triazol-3-yl)propane phosphonic acid (Compound No. 24 in Table I).

A stirred solution of diethyl 3-hydroxy-3(1-trityl-1,2,4-triazol-3-yl)propane phosphonate (1.0 g, prepared as described in Example 24), triethylamine (0.22 g) and 4-dimethylaminopyridine (0.03 g) in dry dichloromethane (10 ml) was treated dropwise with acetic anhydride (0.28 g), whilst maintaining the temperature below 5° C. The mixture was allowed to warm to room temperature, stirred for a further two hours, diluted with dichloromethane, washed with water, dried over magnesium sulphate and evaporated under reduced pressure. The residue was chromatographed on silica, using dichloromethane-ethanol (19:1) as eluant, to give diethyl 3-acetoxy-3(1-trityl-1,2,4-triazol-3-yl)propane phosphonate (0.86 g, m.p. 100°–102° C.). NMR (CDCl$_3$): δ1.3(6H,t), 1.65–1.9(2H,m), 2.1(3H,s), 2.2–2.35(2H,m), 4.05(4H,m), 5.9(1H,t), 7.1(6H,m), 7.3(9H,m), 7.9(1H,s). M/S: M+ 547.

A solution of this material (0.90 g) and trimethylsilyl bromide (2.0 ml) in dichloromethane (10 ml) was allowed to stand for eighteen hours, then evaporated under reduced pressure. The residue was partitioned between chloroform and water, and the aqueous phase washed with ether and concentrated under reduced pressure. This residue was chromatographed on Amberlite CG-120(H+) resin and freeze-dried to give the title compound (0.11 g) as a white gum. NMR (D$_2$O): δ1.3–1.6(2H,m), 2.0(3H,s), 2.05–2.1(2H,m), 5.8(1H,t), 8.4(1H,s). FAB M/S: MH+ 250.

EXAMPLE 27

This Example illustrates the preparation of 3-fluoro-3(1,2,4-triazol-3-yl)propane phosphonic acid (Compound No. 5 in Table 1).

A solution of diethyl 3-hydroxy-3(1-trityl-1,2,4-triazol-3-yl)propane phosphonate (1.0 g, prepared as described in Example 24) in dichloromethane (3 ml) was added dropwise with stirring at −70° C. to a solution of diethylaminosulphur trifluoride (0.37 g) in dichloromethane (7 ml). The mixture was stirred at −70° C. for two hours, allowed to warm to room temperature and, after a further one hour, diluted with dichloromethane, washed with water and sodium bicarbonate solution, dried over magnesium sulphate, and evaporated under reduced pressure. The residue was chromatographed on silica, using dichloromethane-ethanol (19:1) as eluant, to give diethyl 3-fluoro-3(1-trityl-1,2,4-triazol-3-yl)propane phosphonate (0.50 g, m.p. 97°–98° C.). NMR (CDCl$_3$): δ1.3(6H,t), 1.7–2.0(2H,m), 2.1–2.5(2H,m), 4.1(4H,m), 5.5–5.7(1H,m), 7.1–7.3(15H,m), 7.95(1H,s). M/S: M+ 507.

A solution of this material (0.56 g) and trimethylsilyl bromide (4.0 ml) in dry dichloromethane (10 ml) was allowed to stand at room temperature for eighteen hours, then evaporated under reduced pressure. The residue was azeotroped with methanol (3×10 ml) under reduced pressure, then partitioned between water and ether. The aqueous layer was concentrated under reduced pressure, chromatographed on Amberlite CG-120(H+) resin and freeze-dried to give the title compound (0.20 g, m.p. 82°–84° C.). NMR (D$_2$O): δ1.6–1.8(2H,m), 2.1–2.3(2H,m), 5.6–5.8(1H,dt), 8.55(1H,s). FAB M/S: MH+ 210.

EXAMPLE 28

This Example illustrates the preparation of 3-chloro-3(1,2,4-triazol-3-yl)propane phosphonic acid (Compound No. 25 in Table I).

Thionyl chloride (20 ml) was added dropwise to a stirred solution of diethyl 3-hydroxy-3(1-trityl-1,2,4-triazol-3-yl)propane phosphonate (1.0 g, prepared as described in Example 24) in pyridine (10 ml), whilst maintaining the temperature below 5° C. The mixture was allowed to warm to room temperature, stirred for three hours, then evaporated under reduced pressure. The residue was dissolved in ethyl acetate, washed with water and brine, dried over magnesium sulphate and evaporated under reduced pressure. This residue was chromatographed on silica, using dichloromethane-ethanol (49:1) as eluant, to give diethyl 3-chloro-3(1-trityl-1,2,4-triazol-3-yl)propane phosphonate (0.64 g, m.p. 123°–124° C.). NMR (CDCl$_3$): δ1.3(6H,t), 1.8–2.1(2H,m), 2.4–2.6(2H,m), 4.1(4H,m), 5.1(1H,t), 7.1(6H,m), 7.4(9H,m), 7.95(1H,s). M/S: M+ 523,525.

A solution of this material (0.54 g) and trimethylsilyl bromide (3.0 ml) in dry dichloromethane (15 ml) was allowed to stand at room temperature for eighteen hours, then evaporated under reduced pressure. The residue was azeotroped with methanol (3×10 ml) under reduced pressure, then partitioned between water and ether. The aqueous phase was concentrated under reduced pressure, chromatographed on Amberlite CG-120(H+) resin and freeze-dried to give the title compound (0.17 g, m.p. 85° C.). NMR (D$_2$O): δ1.6–1.9(2H,m), 2.3–2.4(2H,m), 5.25(1H,t), 8.6(1H,s). FAB M/S: MH+ 226,228.

EXAMPLE 29

This Example illustrates the preparation of 3-bromo-3(1,2,4-triazol-3-yl)propane phosphonic acid (Compound No. 26 in Table I).

A solution of bromine (0.53 g) in dichloromethane (1 ml) was added dropwise to a solution of tri-n-butylphosphine (0.68 g) in dichloromethane (12 ml), whilst maintaining the temperature below 0° C. The mixture was stirred for ten minutes at this temperature then treated, dropwise with stirring, with a solution of diethyl 3-hydroxy-3(1-trityl-1,2,4-triazol-3-yl)propane phosphonate (1.5 g, prepared as described in Example 24) and triethylamine (0.30 g) in dichloromethane (20 ml), maintaining the temperature below 0° C. It was allowed to warm slowly to room temperature, to stand for two days, then diluted with ethyl acetate, washed with water and brine, dried over magnesium sulphate and evaporated under reduced pressure. The residue was chromatographed on silica, using dichloromethane-ethanol (49:1) as eluant, to give diethyl 3-bromo-3(1-trityl-1,2,4-triazol-3-yl)propane phosphonate (1.27 g, m.p. 108°–110° C.). NMR (CDCl$_3$): δ1.13(6H,dt), 1.6–2.1(2H,m), 2.5–2.6(2H,m), 4.1(4H,m), 5.15(1H,t), 7.1(6H,m), 7.3(9H,m), 7.9(1H,s). M/S: M+ 567,569.

A solution of this material (0.55 g) and trimethylsilyl bromide (3.0 ml) in dry dichloromethane (10 ml) was allowed to stand overnight then evaporated under reduced pressure. The residue was partitioned between water and ether. The aqueous phase was concentrated under reduced pressure, chromatographed on Amberlite CG-120 (H+) resin and freeze-dried to give the title compound (0.060 g, m.p.120° C., dec). NMR (D$_2$O): $\delta$1.4–1.8(2H,m), 2.2–2.4(2H,m), 5.1(1H,t), 8.3(1H,s). FAB M/S: MH+ 270,272.

EXAMPLE 30

This Example illustrates the preparation of 3-iodo-3(1,2,4-triazol-3-yl)propane phosphonic acid (Compound No. 27 in Table I).

A solution of diethyl 3-bromo-3(1-trityl-1,2,4-triazol-3-yl)propane phosphonate (1.0 g, prepared as described in Example 29) and sodium iodide (1.30 g) in acetone (15 ml) was allowed to stand for twenty hours at room temperature in the absence of light. It was then filtered through Hyflo Super-Cel, evaporated under reduced pressure and the residue partitioned between ethyl acetate and water. The organic layer was washed with brine, dried over magnesium sulphate and evaporated under reduced pressure. The residue was chromatographed on silica, using dichloromethane-ethanol (49:1) as eluant, to give diethyl 3-iodo-3(1-trityl-1,2,4-triazol-3-yl)propane phosphonate (0.85 g, m.p. 98°–100° C.). NMR (CDCl$_3$): $\delta$1.3(6H,t), 1.7–1.9(2H,m), 2.5–2.6(2H,m), 4.05(4H,m), 5.3(1H,t), 7.1(6H,m), 7.3(9H,m), 7.9(1H,s). M/S: M+ 615.

A solution of this material (0.75 g) in acetonitrile (5 ml) was treated with trimethylsilyl iodide (5.0 g) and the mixture allowed to stand for eighteen hours in the absence of light. It was then evaporated under reduced pressure and the residue partitioned between water and chloroform. The aqueous layer was washed with ether, concentrated under reduced pressure, chromatographed on Amberlite CG-120(H+) resin and freeze-dried to give the title compound (0.14 g, m.p. 89°–90° C.). NMR (D$_2$O): $\delta$1.5–1.9(2H,m), 2.3–2.5(2H,m), 5.3(1H,t), 8.55(1H,s). FAB M/S: MH+ 318.

The iodoester can also be prepared directly from the hydroxyester by successive treatments with tributylphosphine and iodine, then triethylamine, in dichloromethane; alternatively the chloroester (prepared as described in Example 28) can be treated with sodium iodide in acetone. Attempted deprotection with trimethylsilyl bromide in the usual way gave bromoacid (for alternative preparation of this, see Example 29).

EXAMPLE 31

This Example illustrates the preparation of 3-azido-3(1,2,4-triazol-3-yl)propane phosphonic acid (Compound No. 28 in Table I).

A mixture of diethyl 3-bromo-3(1-trityl-1,2,4-triazol-3-yl)propane phosphonate (1.05 g, prepared as described in Example 29), sodium azide (0.60 g), 15-Crown-5 (0.02 g), water (1.2 ml) and N,N-dimethylformamide (10 ml) was heated at 100° C. for five hours, cooled, poured into water, and extracted with ethyl acetate. The extracts were washed with water and brine, dried over magnesium sulphate, and evaporated under reduced pressure. The residue was chromatographed on silica, using dichloromethane-ethanol (49:1) as eluant, to give diethyl 3-azido-3(1-trityl-1,2,4-triazol-3-yl)propane phosphonate (0.64 g, m.p. 82°–84° C.). NMR (CDCl$_3$): $\delta$1.3(6H,dt), 1.6–2.0(2H,m), 2.2–2.3(2H,m), 4.1(4H,m), 4.65(1H,t), 7.1(6H,m), 7.3(9H,m), 8.0(1H,s). M/S: MH+ 531.

A solution of this material (0.64 g) and trimethylsilyl bromide (3.0 ml) in dry dichloromethane (10 ml) was allowed to stand for eighteen hours, then evaporated under reduced pressure. The residue was partitioned between water and ether, then the aqueous phase extracted with dichloromethane, then ether, and concentrated under reduced pressure. This residue was chromatographed on Amberlite CG-120(H+) resin and freeze-dried to give the title compound (0.10 g) as a white gum. NMR (D$_2$O): $\delta$1.4–1.7(2H,m), 1.9–2.1(2H,m), 4.75(1H,t), 8.45(1H,s). FAB M/S: MH+ 233.

The azidoester can also be prepared by treating other halides, for example the chloride, with azide salts.

EXAMPLE 32

This Example illustrates the preparation of 3(1,2,4-triazol-1-yl)-3(1,2,4-triazol-3-yl)propane phosphonic acid (Compound No. 29 in Table I).

A stirred solution of 1,2,4-triazole (0.15 g) in dry N,N-dimethylformamide (10 ml) was treated, under nitrogen, with sodium hydride (0.075 g, 60% in oil) and 15-Crown-5 (0.02 g). After ten minutes, the stirred mixture was treated with diethyl 3-bromo-3(1-trityl-1,2,4-triazol-3-yl)propane phosphonate (1.0 g, prepared as described in Example 29). After a further three hours, it was poured into water and extracted with ethyl acetate. The extracts were washed with brine, dried over magnesium sulphate and evaporated under reduced pressure, finally at 0.01 mm. The residue was chromatographed on silica, using dichloromethane-ethanol (19:1) as eluant, to give diethyl 3(1,2,4-triazol-1-yl)-3(1-trityl-1,2,4-triazol-3-yl)propane phosphonate (0.39 g) as a colourless oil. NMR (CDCl$_3$): $\delta$1.2(6H,dt), 1.7–1.8(2H,m), 2.6–2.8(2H,m), 4.05(4H,m), 5.7(1H,t), 7.1(6H,m), 7.3(9H,m), 7.95(2H,2xs), 8.25(1H,s). M/S: M+ 556.

A solution of this material (0.39 g) and trimethylsilyl bromide (2.0 ml) in dry dichloromethane (10 ml) was allowed to stand for twenty hours, then evaporated under reduced pressure. Deprotection was incomplete. A suspension of the residue in acetonitrile (10 ml) was retreated with trimethylsilyl bromide (2.0 g) as described above. This residue was azeotroped with methanol (3 × 10 ml) under reduced pressure, partitioned between water and ether and the aqueous phase concentrated under reduced pressure, then chromatographed on Amberlite CG-120(H+) resin to give the title compound (0.40 g) as a sticky solid. NMR(D$_2$O): $\delta$1.3–1.7(2H,m), 2.4–2.6(2H,m), 5.8(1H,t), 8.15(1H,s), 8.4(1H,s), 8.85(1H,s). FAB M/S: MH+ 259.

EXAMPLE 33

This Example illustrates the preparation of 3-cyano-3(1,2,4-triazol-3-yl)propane phosphonic acid (Compound No. 30 in Table I).

A mixture of diethyl 3-bromo-3(1-trityl-1,2,4-triazol-3-yl) propane phosphonate (1.20 g, prepared as described in Example 29), sodium cyanide (0.12 g) and 15-Crown-5 (0.03 g) in dry N,N-dimethylformamide (15 ml) was stirred for eighteen hours at room temperature. It was evaporated under reduced pressure and the residue partitioned between water and ethyl acetate. The organic phase was washed with water, then brine, dried over magnesium sulphate and evaporated under reduced pressure. This residue was chromatographed on silica, using dichloromethane-ethanol (49:1) as eluant, to give diethyl 3-cyano-3(1-trityl-1,2,4-triazol-3-yl)propane phosphonate (0.83 g) as a pale yellow oil. NMR (CDCl$_3$): $\delta$1.3(6H,t), 1.8–2.0(2H,m), 2.3–2.4(2H,m), 4.05(4H,m), 4.2(1H,t), 7.1(6H,m), 7.3(9H,m), 7.95(1H,s). M/S: M+ 514.

A solution of this material (0.80 g) and trimethylsilyl bromide (2.0 ml) in dry dichloromethane (10 ml) was allowed to stand for twenty hours, then evaporated under reduced pressure. The residue was partitioned between water and chloroform, the aqueous phase washed with ether then evaporated under reduced pressure. The residue was chromatographed on Amberlite CG-120(H+) resin to give the title compound (0.10 g, m.p. 87°–89° C.). NMR (D$_2$O): $\delta$1.4–1.6(2H,m), 2.05–2.2(2H,m), 4.6(1H,t), 8.3(1H,s). FAB M/S: MH+ 217.

EXAMPLE 34

This Example illustrates the preparation of 3-nitrosyloxy-3(1,2,4-triazol-3-yl)propane phosphonic acid (Compound No. 31 in Table I).

Silver nitrite (1.35 g) was added to a solution of diethyl 3-bromo-3(1-trityl-1,2,4-triazol-3-yl)propane phosphonate (1.0 g, prepared as described in Example 29) in dry ether (50 ml) and the mixture stirred vigoursly for twenty hours in the absence of light. It was then poured into water and extracted with ethyl acetate. The organic phases were washed with brine, dried over magnesium sulphate, and evaporated under reduced pressure. The residue was chromatographed on silica, using dichloromethane-ethanol (49:1) as eluant, to give diethyl 3-nitrosyloxy-3-(1-trityl-1,2,4-triazol-3-yl)propane phosphonate (0.55 g) as a sticky solid. NMR(CDCl$_3$): $\delta$1.3(6H,t), 1.7–1.9(2H,m), 2.3–2.4(2H,m), 4.05(4H,m), 6.05(1H,t), 7.1(6H,m), 7.3(9H,m), 7.95(1H,s). IR: 1640 cm$^{-1}$ (no NO$_2$ peaks).

A solution of this material (0.64 g) and trimethylsilyl bromide (2.0 ml) in dichloromethane (5 ml) was allowed to stand overnight, then evaporated under reduced pressure. The residue was partitioned between chloroform and water and the aqueous phase washed with ether and concentrated under reduced pressure. This residue was chromatographed on Amberlite CG-120(H+) resin to give the title compound (0.10 g, m.p. 92° C.). NMR (D$_2$O): $\delta$ 1.5–1.8(2H,m), 2.1–2.3(2H,m), 6.1(1H,t), 8.5(1H,s). FAB M/S: Decomposition.

EXAMPLE 35

This Example illustrates the preparation of 3-aminoxy-3(1,2,4-triazol-3-yl)propane phosphonic acid (Compound No. 32 in Table 1).

A stirred solution of t-butyl-N-hydroxycarbamate (0.25 g) in ethanol (10 ml) was treated with postassium hydroxide (0.10 g), then diethyl 3-bromo-3(1-trityl-1,2,4-triazol-3-yl)propane phosphonate (1.0 g, prepared as described in Example 29) added. The mixture was allowed to stand for twenty hours, poured into ice-water, neutralized with a little acetic acid and extracted with ethyl acetate. The extracts were washed with brine, dried over magnesium sulphate, and evaporated under reduced pressure to give crude diethyl 3-t-butoxycarbonylaminoxy-3(1-trityl-1,2,4-triazol-3-yl)propane phosphonate (1.14 g) as a colourless gum. NMR (CDCl$_3$): $\delta$ 1.3(6H,t), 1.4(9H,s), 1.5–1.8(2H,m), 2.2–2.3(2H,m), 4.1(4H,m), 5.0(1H,t), 7.1(6H,m), 7.3(9H,m), 7.95(1H,s). M/S: M+ 620.

A solution of this material (1.14 g) and trimethylsilyl bromide (2.0 ml) in dry dichloromethane (10 ml) was allowed to stand for twenty hours, then evaporated under reduced pressure. The residue was partitioned between chloroform and water, and the aqueous phase washed with ether then evaporated under reduced pressure. This residue was chromatographed on Amberlite CG-120(H+) resin, using water then 0.5M ammonium hydroxide as eluants, with appropriate fractions being freeze-dried to give the title compound (0.05 g) as a white gum. NMR (D$_2$O): $\delta$1.0–1.3(2H,m), 1.8–2.0(2H,m), 4.7(1H,m), 8.2(1H,s). FAB M/S: MH+ 223.

EXAMPLE 36

This Example illustrates the preparation of 3(ethoxythiocarbonylthio)-3(1,2,4-triazol-3-yl)propane phosphonic acid (Compound No. 33 in Table 1).

A stirred solution of 18-Crown-6 (0.03 g) in dry tetrahydrofuran (25 ml) was treated successively with potassium ethylxanthate (0.44 g) and diethyl 3-bromo-3(1-trityl-1,2,4-triazol-3-yl)propane phosphonate (1.0 g, prepared as described in Example 29). The mixture was allowed to stand for two days, poured into water and extracted with ethyl acetate. The extracts were washed with brine, dried over magnesium sulphate, and evaporated under reduced pressure. The residue was chromatographed on silica, using dichloromethane-ethanol (49:1) as eluant, to give diethyl 3(ethoxythiocarbonylthio)-3(1-trityl-1,2,4-triazol-3-yl)propane phosphonate (0.86 g) as a colourless gum. NMR(CDCl$_3$): $\delta$1.25(6H,m), 1.4(3H,t), 1.7–1.9(2H,m), 2.3–2.4(2H,m), 4.0(4H,m), 4.6(2H,m), 5.05(1H,t), 7.1(6H,m), 7.3(9H,m), 7.9(1H,S). M/S: M+ 609.

A solution of this material (0.80 g) and trimethylsilyl bromide (2.0 ml) in dichloromethane (15 ml) was allowed to stand for twenty hours, then evaporated under reduced pressure. The residue was partitioned between chloroform and water and the aqueous phase washed with ether, concentrated under reduced pressure, chromtographed on Amberlite CG-120 (H+) resin and freeze-dried to give title compound (0.07 g, m.p. 78°–80° C.) of 85% purity. NMR(D$_2$O): $\delta$1.2(3H,t), 1.4–1.8(2H,m), 2.1–2.2(2H,m), 4.5(2H,m), 5.0(1H,t), 8.5(1H,s). FAB M/S: MH+ 312. The presence of the second component (e.g. NMR: $\delta$5.2, 1H?) was confirmed by $^{31}$p NMR but its structure was not established.

EXAMPLE 37

This Example illustrates the preparation of 3-acetylthio-3(1,2,4-triazol-3-yl)propane phosphonic acid (Compound No. 34 in Table 1).

A stirred solution of 18-crown-6 (0.04 g) in dry tetrahydrofuran (25 ml) was treated successively with potassium thiolacerate (0.59 g) and diethyl 3-bromo-3(1-trityl-1,2,4-triazol-3-yl)propane phosphonate (1.94 g, prepared as described in Example 29). The mixture was allowed to stand for two days, poured into water and extracted with ethyl acetate. The extracts were washed with brine, dried over magnesium sulphate and evaporated under reduced pressure. The residue was chromatographed on silica, using dichloromethane-ethanol (49:1) as eluant, to give diethyl 3-acetylthio-3(1-trityl-1,2,4-triazol-3-yl)propane phosphonate (1.51 g) as a pale yellow oil. NMR(CDCl$_3$): $\delta$1.3(6H,m), 1.6–1.9(2H,m), 2.2–2.3(2H,m), 2.4(3H,s), 4.0(4H,m), 4.9(1H,t), 7.15(6H,m), 7.3(9H,m), 7.9(1H,s), M/S: M+ 563.

A solution of this material (0.70 g) and trimethylsilyl bromide (2.0 ml) in dichloromethane (10 ml) was allowed to stand for eighteen hours at room temperature, then evaporated under reduced pressure. The residue was partitioned between chloroform and water and the aqueous phase concentrated under reduced pressure, chromatographed on Amberlite CG-120(H+) resin and freeze-dried to give the title compound (0.06 g, m.p. 142°–143° C.). NMR(D$_2$O): δ1.4–1.7 (2H,m), 2.05–2.2 (2H,m), 2.25(3H,s), 4.7(1H,t), 8.5(1H,s). FAB M/S: MH+ 266.

EXAMPLE 38

This Example illustrates the preparation of 3-mercapto-3(1,2,4-triazol-3-yl)propane phosphonic acid (Compound No. 35 in Table 1).

A solution of diethyl 3-acetylthio-3(1-trityl-1,2,4-triazol-3-yl)propane phosphonate (0.71 g, prepared as described in Example 37) in methanol (20 ml) was added dropwise, under nitrogen, to a stirred solution of sodium methoxide (from 0.06 g sodium) in methanol (10 ml), whilst maintaining the temperature below 5° C. The mixture was allowed to attain room temperature and to stand for twenty hours, neutralized with solid carbon dioxide, poured into water and extracted with ethyl acetate. The extracts were washed with water and brine, dried over magnesium sulphate and evaporated under reduced pressure. The residue was chromatographed on silica, using dichloromethane-ethanol (49:1) as eluant, to give diethyl 3-mercapto-3(1-trityl-1,2,4-triazol-3-yl)propane phosphonate (0.35 g) as a colourless gum. NMR (CDCl$_3$): δ1.3(6H,dt), 1.7–2.0(2H,m), 2.2–2.4(2H,m), 4.0(4H,m), 4.1(1H,m), 7.1(6H,m), 7.3(9H,m), 7.9(1H,s). M/S: M+ 521.

A solution of this material (0.69 g) and trimethylsilyl bromide (2.0 ml) in dichloromethane (10 ml) was allowed to stand under nitrogen for twenty hours, then evaporated under reduced pressure. The residue was partitioned between chloroform and water, and the aqueous phase concentrated under reduced pressure, chromatographed on Amberlite CG-120(H+) resin and freeze-dried to give the title compound (0.06 g, m.p. 253° C., dec.). NMR (D$_2$O): δ1.5–1.8(2H,m), 2.1–2.4(2H,m), 4.25(1H,t), 8.6(1H,s). FAB M/S: MH+ 224.

EXAMPLE 39

This Example illustrates the preparation of 3-methylthio-3(1,2,4-triazol-3-yl)propane phosphonic acid (Compound No. 36 in Table I).

Sodium thiomethoxide (0.24 g) was added to a stirred solution of diethyl 3-iodo-3(1-trityl-1,2,4-triazol-3-yl)propane phosphonate (1.0 g, prepared as described in Example 30) in ethanol (10 ml). The mixture was stirred for five hours, allowed to stand overnight, poured into water and extracted with ethyl acetate. The extracts were washed with brine, dried over magnesium sulphate and evaporated under reduced pressure. The residue was chromatographed on silica, using dichloromethane-ethanol (49:1) as eluant, to give diethyl 3-methylthio-3(1-trityl-1,2,4-triazol-3-yl)propane phosphonate (0.60 g, m.p. 97°–98° C.). NMR (CDCl$_3$): δ1.3(6H,dt), 1.7–1.9(2H,m), 1.9(3H,s), 2.2–2.4(2H,m), 3.9(1H,t), 4.05(4H,m), 7.1(6H,m), 7.3(9H,m), 7.9(1H,s). FAB M/S: MH+ 536.

A solution of this material (0.55 g) and trimethylsilyl bromide (2.0 ml) in dry dichloromethane (10 ml) was allowed to stand for twenty hours, then evaporated under reduced pressure. The residue was partitioned between chloroform and water and the aqueous phase washed with ether and concentrated under reduced pressure. This residue was chromatographed on Amberlite CG-120(H+) resin and freeze-dried to give the title compound (0.12 g) as a colourless gum. NMR (D$_2$O): δ1.4–1.8(2H,m), 1.9(3H,s), 2.05–2.2(2H,m), 4.05(1H,t), 8.6(1H,s). FAB M/S: MH+ 238.

EXAMPLE 40

This Example illustrates the preparation of 3-methanesulphinyl-3(1,2,4-triazol-3-yl)propane phosphonic acid (Compound No. 37 of Table I) as 75% of a 2:1 mixture of diastereoisomers and 25% of the methylthio acid.

A solution of diethyl 3-methylthio-3(1-trityl-1,2,4-triazol-3-yl)propane phosphonate (0.53 g, prepared as described in Example 39) in methanol (7 ml) was added slowly to a stirred solution of sodium periodate (0.23 g) in water (3 ml) cooled to 5° C. After ten minutes, the cooling bath was removed and stirring continued for a further five hours. The mixture was poured into water and extracted with ethyl acetate. The extracts were washed with brine, dried over magnesium sulphate, and evaporated under reduced pressure to give diethyl 3-methanesulphinyl-3(1-trityl-1,2,4-triazol-3-yl)propane phosphonate (0.59 g, white gum) as a 2:1 mixture of diastereoisomers. NMR (CDCl$_3$): δ1.3(6H,m), 1.7–1.9(2H,m), 2.4(3H,2xs), 2.5–2.7(2H,m), 4.05(5H,m), 7.1–7.3(15H,m), 8.0(1H,2xs).

This material (0.61 g) was deprotected as described in Example 39 to give the title compound (0.114 g, white gum), as a 2:1 diastereoisomeric mixture (75% of total), together with 25% of the methylthio acid described in Example 39. NMR (D$_2$O): δ1.5–1.9(2H,m), 2.1–2.4(2H,m), 2.45(3H,2xs), 4.25(0.5H,dd), 4.45(0.5H,dd), 8.5(1H,2xs). FAB M/S: MH+ 254.

EXAMPLE 41

This Example illustrates the preparation of 3-methanesulphonyl-3-(1,2,4-triazol-3-yl)propane phosphonic acid (Compound No. 38 of Table I).

A solution of m-chloroperbenzoic acid (0.28 g, 50% water) in dichloromethane was dried over magnesium sulphate, then evaporated under reduced pressure. The residue (0.14 g) was added to a stirred solution of diethyl 3-methylthio-3(1-trityl-1,2,4-triazol-3-yl)propane phosphonate (0.2 g, prepared as described in Example 39) in dichloromethane (15 ml). After three hours, the mixture was diluted with dichloromethane, washed with saturated sodium bicarbonate solution and dried over magnesium sulphate. Evaporation under reduced pressure gave diethyl 3-methanesulphonyl-3(1-trityl-1,2,4-triazol-3-yl)propane phosphonate (0.21 g) as a white gum. NMR (CDCl$_3$): δ1.3(6H,2xt), 1.7–1.85(2H,m), 2.5–2.7(2H,m), 2.85(3H,s), 4.05(4H,m), 4.4(1H,2xd), 7.1–7.3(15H,m), 8.0(1H,s). M/S: M+ 567.

This material (0.38 g) was deprotected as described in Example 39 to give the title compound (0.04 g) as a white gum. NMR (D$_2$O): δ 1.6–1.8(2H,m), 2.4–2.6(2H,m), 3.0(3H,s), 4.8(1H,m), 8.6(1H,s). FAB M/S: MH+ 270.

EXAMPLE 42

This Example illustrates the preparation of 3-oxo-3(1,2,4-triazol-3-yl)propane phosphonic acid (Compound No. 6 in Table 1).

A solution of dimethylsulphoxide (0.46 g) in dichloromethane (3 ml) was added dropwise to a stirred solution of oxalyl chloride (0.36 g) in dichloromethane (15 ml), maintaining the temperature below −60° C. After fifteen minutes, a solution of diethyl 3-hydroxy-3(1-trityl-1,2,4-triazol-3-yl)propane phosphonate (1.19 g, prepared as described in Example 24) in dichloromethane (5 ml) was added, dropwise with stirring, at −60° C. After a further one hour, triethylamine (4.0 ml) was added. The stirred reaction mixture was allowed to warm to −25° C. over fifteen minutes, maintained at that temperature for fifteen minutes, then treated with ether (25 ml) and water (25 ml). The aqueous phase was reextracted twice with ethyl acetate and the combined organic layers washed with water and brine, dried over magnesium sulphate and evaporated under reduced pressure. The residue was chromatographed on silica, using dichloromethane-ethanol (19:1) as eluant, to give diethyl 3-oxo-3(1-trityl-1,2,4-triazol-3-yl)propane phosphonate (0.87 g, m.p. 99°–100° C.). NMR (CDCl$_3$): $\delta$1.25(6H,t), 2.1–2.25(2H,m), 3.35(2H,m), 4.1(4H,m), 7.1–7.35(15H,m), 8.05(1H,s). M/S: M+ 503. IR: 1712 cm$^{-1}$.

A solution of this material (0.55 g) and trimethylsilyl bromide (4 ml) in dry dichloromethane (10 ml) was allowed to stand at room temperature for two days. It was evaporated under reduced pressure, azeotroped with methanol (3×10 ml) under reduced pressure, and the residue partitioned between water and ether. The aqueous phase was concentrated under reduced pressure, then chromatographed on Amberlite CG-120(H+) resin, using water as eluant, and freeze-dried to give the title compound (0.18 g, m.p. 213°–215° C.). NMR (D$_2$O): $\delta$2.0(2H,m), 3.3(2H,m), 8.5(1H,s). FAB M/S: (M+Na)+ 228.

EXAMPLE 43

This Example illustrates the preparation of 3,3-difluoro-3(1,2,4-triazol-3-yl)propane phosphonic acid (Compound No. 39 in Table I).

Diethyl 3-oxo-3(1-trityl-1,2,4-triazol-3-yl)propane phosphonate (0.98 g, prepared as described in Example 42) was added to stirred diethylaminosulphur trifluoride (5 ml). The eventual solution was allowed to stand overnight, diluted with dichloromethane (50 ml) and added dropwise to stirred ice-cooled sodium hydroxide solution (2M, 30 ml). Dichloromethane extracts were washed with brine, dried over magnesium sulphate and evaporated under reduced pressure. The residue was chromatographed on silica, using dichloromethane-ethanol (49:1) as eluant, to give diethyl 3,3-difluoro-3(1-trityl-1,2,4-triazol-3-yl)propane phosphonate (0.39 g, m.p. 70° C.). NMR (CDCl$_3$): $\delta$1.3(6H,t), 1.85–2.0(2H,m), 2.5–2.7(2H,m), 4.05(4H,m), 7.1–7.35(15H,m), 8.0(1H,s). M/S: M+ 525.

A solution of this material (0.39 g) and trimethylsilyl bromide (2.0 ml) in dichloromethane (10 ml) was allowed to stand overnight, then evaporated under reduced pressure. The residue was partitioned between chloroform and water. The aqueous phase was washed with ether, concentrated under reduced pressure, chromatographed on Amberlite CG-120(H+) resin and freeze-dried to give the title compound (0.06 g) as a pale yellow gum. NMR (D$_2$O): $\delta$ 1.55–1.70(2H,m), 2.3–2.5(2H,m), 8.4(1H,s). FAB M/S: MH+ 228.

EXAMPLE 44

This Example illustrates the preparation of 3-oximino-3(1,2,4-triazol-3-yl)propane phosphonic acid (Compound No. 7 in Table I).

Hydroxylamine hydrochloride (0.29 g), then pyridine (7.7 ml), was added under nitrogen to a stirred solution of diethyl 3-oxo-3(1-trityl-1,2,4-triazol-3-yl)propane phosphonate (1.0 g, prepared as described in Example 42) in ethanol (20 ml). The mixture was stirred at room temperature for three hours, then evaporated under reduced pressure. The residue was treated with water, basified to pH 8 with 1M sodium hydroxide solution, and extracted with chloroform. The organic layers were washed with brine, dried over magnesium sulphate and evaporated under reduced pressure. The residue was chromatographed on silica, using dichloromethane-ethanol (19:1) as eluant, to give diethyl 3-oximino-3(1-trityl-1,2,4-triazol-3-yl)propane phosphonate (0.90 g, m.p. 190°–192° C.), probably as a single geometric isomer of unknown configuration. NMR (CDCl$_3$): $\delta$1.2(6H,t), 1.95–2.1(2H,m), 3.05(2H,m), 3.95(4H,m), 7.1–7.3(15H,m), 8.0(1H,s), 9.1(1H,br).

A solution of the above compound (1.02 g) and trimethylsilyl bromide (4 ml) in dichloromethane (10 ml) was allowed to stand for eighteen hours at room temperature, then evaporated under reduced pressure. The residue was partitioned between ether and water, which was then basified to pH9 with 2M sodium hydroxide solution. The aqueous layer was chromatographed on Amberlite CG-120(H+) resin, eluting first with water, then 0.5M ammonium hydroxide solution to give, after freeze drying, the title compound (0.28 g, m.p. 211° C. dec). NMR (D$_2$O): $\delta$1.45(2H,m), 2.7(2H,m), 8.2(1H,s). FAB M/S: MH+ 221.

EXAMPLE 45

This Example illustrates the preparation of 3-amino-3(1,2,4-triazol-3-yl)propane phosphonic acid (Compound No. 8 in Table I).

A solution of diethyl 3-azido-3(1-trityl-1,2,4-triazol-3-yl)propane phosphonate (0.74 g, prepared as described in Example 31) in isopropanol (10 ml) was hydrogenated over 10% palladium on carbon (0.05 g). When all starting material had been consumed (TLC), the reaction mixture was filtered through Hyflo Super-Cel and evaporated under reduced pressure. The residue was chromatographed on silica, using dichloromethane-ethanol (19:1) then dichloromethane-ethanol (1:1) as eluants, to give diethyl 3-amino(1-trityl-1,2,4-triazol-3-yl)propane phosphonate (0.48 g) as a gum. NMR (CDCl$_3$): $\delta$1.3(6H,t), 1.7–1.9(2H,m), 2.1–2.2(2H,m), 4.05(4H,m), 4.2(1H,t), 7.1–7.3(15H,m), 7.95(1H,s). M/S: M+ 504.

The aminoester can also be prepared by reductive amination of the corresponding ketone. Thus, ammonium acetate (0.31 g) and sodium borohydride (0.18 g) were added to a stirred solution of diethyl 3-oxo-3(1-trityl-1,2,4-triazol-3-yl)propane phosphonate (0.20 g, prepared as described in Example 42) in methanol (5 ml). The mixture was allowed to stir for four hours, acidified to pH2 with 2M hydrochloric acid, basified with 2M sodium hydroxide solution, and extracted with dichloromethane. The extracts were washed with brine, dried over magnesium sulphate and evaporated under reduced pressure. The residue was purified as described above to give the aminoester (0.03 g) as a gum.

A solution of the amino ester (0.48 g) and trimethylsilyl bromide (2.0 ml) in dry dichloromethane (10 ml) was allowed to stand for twenty hours. It was evaporated under reduced pressure, partitioned between water and dichloromethane, and the aqueous layer concentrated under reduced pressure. The residue was chromatographed on Amberlite CG-120(H+) resin using water, then 0.5M ammonium hydroxide, as eluants. Appropriate fractions were freeze-dried to give the title compound (0.11 g, m.p. 200°–201° C.). NMR (D$_2$O): δ1.2–1.4(2H,m), 2.0–2.2(2H,m), 4.3(1H,t), 8.3(1H,s). FAB M/S: MH+ 207.

EXAMPLE 46

This Example illustrates the preparation of diethyl 3(1-trityl-1,2,4-triazol-3-yl)propa-1,2-diene phosphonate having the structural formula (XX).

n-Butyllithium (18.5 ml, 1.6M in hexane) was added dropwise with stirring under nitrogen, to a solution of trimethylsilylacetylene (4.2 ml) in dry tetrahydrofuran (60 ml) whilst maintaining the temperature below −60° C. After a further thirty minutes, the mixture was treated, dropwise with stirring at <−60° C. with a solution of 1-trityl-1,2,4-triazole 3-carboxaldehyde (10.0 g, prepared as described in Example 3) in dry dichloromethane (30 ml). After a further fifteen minutes at −60° C., the mixture was allowed to warm to −20° C. over thirty minutes, then quenched into a mixture of saturated ammonium chloride solution (100 ml) and ethyl acetate (200 ml). The organic layer was washed with water (50 ml) and brine (100 ml), dried over magnesium sulphate, and evaporated under reduced pressure to give crude 1-trimethylsilyl-3(1-trityl-1,2,4-triazol-3-yl)-prop-1-yn-3-ol as a brown oil. A solution of this material and potassium fluoride (3.5 g) in methanol (200 ml) was allowed to stand at room temperature for eighteen hours, evaporated under reduced pressure and the residue partitioned between dichloromethane (200 ml) and brine (100 ml). The organic layer was dried over magnesium sulphate, evaporated under reduced pressure and the residue chromatographed on silica, using dichloromethane-ether (3:1) as eluant, to give 3(1-trityl-1,2,4-triazol-3-yl)prop-1-yn-3-ol (5.9 g, m.p. 138°–139° C.). NMR (CDCl$_3$): δ2.59(1H,d), 4.35(1H,d), 5.68(1H,dd), 7.1–7.4(15H,m), 7.95(1H,s).

A stirred solution of diethylchlorophosphite (4.5 ml) in dichloromethane (50 ml) was cooled to below 5° C. under nitrogen, treated with triethylamine (4.3 ml) and 4-dimethylaminopyridine (0.056 g), then dropwise with a solution of the above acetylenic alcohol (5.53 g) in dichloromethane (20 ml) whilst maintaining the temperature below 5° C. The mixture was stirred at 5° C. for ten minutes, then allowed to warm to room temperature over thirty minutes. After a further ninety minutes, it was diluted with dichloromethane (200 ml) and washed with water (2×75 ml). The organic layer was dried over magnesium sulphate, evaporated under reduced pressure and chromatographed on silica, using chloroform-methanol (50:1) as eluant, to give the title compound (5.9 g) as an oil, which solidified on storage at 0° C., apparently as a single stereoisomer. NMR (CDCl$_3$): δ1.3(6H,t), 4.18(4H,m), 5.8(1H,dd), 6.8(1H,dd), 7–7.4(15H,m), 7.9(1H,s). IR: 1957 cm$^{-1}$. Structure confirmed by $^{13}$C NMR.

In an alternative procedure, a solution of diethyl 3(1-trityl-1,2,4-triazol-3-yl)prop-2-yne phosphonate (0.31 g, prepared as described in Example 17) in ethyl acetate was passed through a column of basic alumina. A quantitative yield of the allene was achieved.

EXAMPLE 47

This Example illustrates the preparation of 2-hydroxy-3(1,2,4-triazol-3-yl)propane phosphonic acid (Compound No. 9 in Table 1).

Sodium hydride (0.6 g, 60% dispersion in mineral oil) was added portionwise to a stirred and cooled solution of diethyl 3(1-trityl-1,2,4-triazol-3-yl)propa-1,2-diene phosphonate (5.9 g, prepared as described in Example 46) in ethanol (150 ml). The solution was allowed to stand for eighteen hours at room temperature, evaporated under reduced pressure and the residue partitioned between dichloromethane (200 ml) and water (150 ml). The organic layer was washed with brine (100 ml), dried over magnesium sulphate and evaporated under reduced pressure to give an oil. This was chromatographed, using chloroform-methanol (25:1) as eluant, to give pure diethyl 2-ethoxy-3-(1-trityl-1,2,4-triazol-3-yl)prop-2-ene phosphonate (2.9 g), possibly as a mixture of geometric isomers. A further sample (4.5 g) was less pure. NMR (CDCl$_3$): δ1.2(6H,t), 1.35(3H,m), 3.65(2H,d), 4.0(6H,m), 5.75(1H,d), 7.1–7.4(15H,m), 7.85(1H,s).

A solution of this enol ether (4.5 g) in ethyl acetate (100 ml) was treated with concentrated hydrochloric acid (45 ml) and the mixture stirred for thirty minutes at room temperature. Excess solid sodium bicarbonate was added portionwise and the liquid decanted off. The residual slurry was extracted with ethyl acetate (2×100 ml). The combined organic layers were dried over magnesium sulphate, evaporated under reduced pressure, and the residue azeotroped with toluene.

A stirred solution of this crude ketonic material in methanol (50 ml) was treated portionwise with sodium borohydride (0.7 g). After a further thirty minutes at room temperature, the solution was evaporated under reduced pressure, then azeotroped under reduced pressure with methanol (2×50 ml). A suspension of the residue in 2N hydrochloric acid (50 ml) was stirred for fifteen minutes, then extracted with toluene (2×50 ml). The aqueous layer was neutralised with solid sodium bicarbonate, then evaporated under reduced pressure. The residue was azeotroped under reduced pressure with ethanol (2×50 ml), then extracted with chloroform-methanol (8:1, 225 ml). The extracts were filtered, evaporated under reduced pressure and the residue chromatographed on silica, using dichloromethane-ethanol-ammonium hydroxide (75:10:1) as eluant, to give diethyl 2-hydroxy-3(1,2,4-triazol-3-yl)propane phosphonate (0.5 g) as a pale yellow oil. NMR (CD$_3$OD): δ1.4(6H,t), 2.2(2H,m), 3.1(2H,m), 4.2(4H,2xd), 4.45(1H,m), 8.25(1H,s).

A solution of this material (0.5 g) in dichloromethane (50 ml) was treated with trimethylsilyl bromide (2 ml) and allowed to stand for eighteen hours at room temperature. It was then evaporated under reduced pressure and the residue azeotroped under reduced pressure with methanol (4×30 ml), then partitioned between water (60 ml) and toluene (30 ml). The aqueous layer was evaporated under reduced pressure, then chromatographed on Amberlite CG-120(H+) resin, using first water then 0.5M ammonium hydroxide as eluant. Appropriate fractions were evaporated under reduced pressure to give the title compound (0.175 g) as an oil. NMR (D$_2$O): δ1.9(2H,m), 2.95–3.25(2H,m), 4.35(1H,m), 8.20(1H,s). FAB M/S: M+ 207.

EXAMPLE 48

This Example illustrates the preparation of (2RS,3SR)-2,3-dihydroxy-3 (1,2,4-triazol-3-yl)propane phosphonic acid (Compound No. 10 in Table 1).

A mixture of diisopropyl E-3(1-trityl-1,2,4-triazol-3-yl)prop-2-ene phosphonate (10.31 g, prepared as described in Example 15), N-methyl-morpholine N-oxide (4.69 g) and osmium tetroxide (2.5 ml, 2.5% in t-butanol) in t-butanol-tetrahydrofuran-water (10:3:1, 350 ml) was stirred at room temperature, under nitrogen, for eight hours. Sodium dithionite (10 g) and water (75 ml) were added, the mixture stirred for thirty minutes, filtered and evaporated under reduced pressure. The residue was made weakly acidic with 2M hydrochloric acid, then partitioned between ethyl acetate and brine. The aqueous layer was reextracted with ethyl acetate and the combined organic layers washed with brine, dried over magnesium sulphate and evaporated under reduced pressure. Chromatography on silica, using dichloromethane-ethanol (12:1) as eluant, gave diisopropyl (2RS,3SR)-2,3-dihydroxy-3(1-trityl-1,2,4-triazol-3-yl)propane phosphonate (8.46 g, m.p. 148°–151° C.), 99% pure by GC. NMR (CDCl$_3$): $\delta$1.3(12H,m), 1.88–2.15(2H,m), 3.7(1H,d), 4.13(1H,d), 4.33(1H,m), 4.6–4.8(3H,m), 7.1–7.4(15H,m), 7.95(1H,s). EI M/S: M+ 549. CI M/S: MH+ 550.

A mixture of this material (1.10 g), tetrahydrofuran (25 ml) and acetic acid-water (1:1, 50 ml) was stirred at room temperature for three days, diluted with water (150 ml) and extracted with ethyl acetate (3×50 ml). The aqueous layer was evaporated under reduced pressure and the residue azeoproped under reduced pressure with toluene to give diisopropyl (2RS,3SR)-2,3-dihydroxy-3(1,2,4-triazol-3-yl)propane phosphonate (0.44 g), m.p. 58°–59° C., 100% pure by GC. NMR (CDCl$_3$): $\delta$1.3(12H,m), 2.15(2H,dd), 4.4(1H,m), 4.7(2H,m), 4.9(1H,d), 7.97(1H,s). EI M/S: M+ 307. CI M/S: MH+ 308.

A stirred solution of this material (0.83 g) in dry dichloromethane (50 ml) was treated under nitrogen with trimethylsilyl bromide (7.13 ml). The mixture was allowed to stand for three days at room temperature, evaporated under reduced pressure, and the residue azeotroped under reduced pressure with methanol (2×25 ml). The residue was chromatographed on Amberlite CG-120(H+), resin, using water as eluant, to give after freeze-drying the title compound (0.52 g, m.p. 120°–123° C. dec). NMR (D$_2$O): $\delta$1.65–2.0(2H,m), 4.15(1H,m), 4.97(1H,d), 8.67(1H,s). (No internal standard, solvent signal at $\delta$4.64). FAB M/S: M+ 223.

EXAMPLE 49

This Example illustrates the preparation of (2RS,3SR)-2,3-epoxy-3-(1,2,4-triazol-3-yl)propane phosphonic acid (Compound No. 11 in Table 1).

A stirred solution of E-3(1,2,4-triazol-3-yl)prop-2-ene phosphonic acid (0.28 g, prepared as described in Example 18) in water (15 ml) was treated with dimethyldioxirane (75 ml, 0.04M in acetone) at 0° C. The mixture was allowed to stand for twenty hours at room temperature, evaporated under reduced pressure, freeze-dried and chromatographed on Amberlite CG-120(H+) resin, using water as eluant. Appropriate fractions were combined and freeze-dried to give a mixture (0.14 g, m.p. 169°–170° C. dec) of the title compound and its hydrolysis product, the 2RS,3RS diol, in a ratio of 7:3, together with traces of the 2RS,3SR diol. NMR (D$_2$O): $\delta$1.85–2.1(2H,m), 3.5(1H,m), 3.98(1H,d), 8.77(1H,s). (No internal standard, solvent signal at $\delta$4.63; only epoxide signals listed).

EXAMPLE 50

This Example illustrates the preparation of (2RS,3RS)-2,3-dihydroxy-3(1,2,4-triazol-3-yl)propane phosphonic acid (Compound No. 12 in Table 1).

A solution of E-3(1,2,4-triazol-3-yl)prop-2-ene phosphonic acid (0.30 g, prepared as described in Example 18) was oxidised with dimethyldioxirane as described in Example 49. The mixture was evaporated under reduced pressure, freeze-dried and the residue dissolved in 1M sodium hydroxide (5 ml). Having been allowed to stand for eighteen hours at room temperature, it was freeze-dried and chromatographed on Amberlite CG-120(H+) resin. Appropriate fractions were freeze-dried to give the title compound (0.055 g, m.p. 97°–100° C. dec). NMR (D$_2$O): $\delta$1.8–2.15(2H,m), 4.34(1H,m), 5.02(1H,d), 8.85(1H,s). FAB M/S: MH+ 224.

EXAMPLE 51

This Example illustrates the preparation of diisopropyl (2RS,3SR)-2,3-epoxy-3(1-trityl-1,2,4-triazol-3-yl)propane phosphonate having the structural formula (XXI).

A solution of dimethyldioxirane (180 ml, 0.04M in acetone) was added to a solution of diisopropyl E-3(1-trityl-1,2,4-triazol-3-yl)prop-2-ene phosphonate (3.70 g, prepared as described in Example 15) in dry acetone (50 ml) under nitrogen. The solution was allowed to stand for eighteen hours at room temperature and evaporated under reduced pressure. The crude product contained residual alkene so it was retreated with dioxirane to give the title compound (3.80 g, m.p. 149°–151° C.). NMR (CDCl$_3$): $\delta$ 1.38(12H,m), 1.95–2.45(2H,m), 3.83(1H,m), 3.93(1H,d), 4.73(2H,m), 7.1–7.4(15H,m), 7.93(1H,s). M/S: M+ 531.

The epoxidation can also be carried out using dimethyl dioxirane, or methyltrifluoromethyl dioxirane, generated in situ.

To a well-stirred mixture of the alkene (8.25 g), dichloromethane (200 ml), acetone (100 ml), phosphate buffer (pH 7.4, 100 ml) and 18-crown-6 (0.79 g) was added, at 0° C. dropwise over thirty minutes, a solution of potassium peroxymonosulphate sold under the trade name 'OXONE' (196.7 g) in water (700 ml). pH was continuously adjusted to 7–8 by addition of 4M sodium hydroxide solution. The mixture was stirred overnight at room temperature, then treated with more acetone/OXONE $^R$/alkali and allowed to stir for a further eighteen hours. This procedure was repeated three times more, by which time essentially all of the alkene had been consumed. The mixture was diluted with water and extracted with dichloromethane (3×150 ml). The extracts were washed with water, dried over magnesium sulphate and evaporated to give pure epoxide (6.29 g).

Alternatively, the reaction was repeated, on the same scale, using 1,1,1-trifluoroacetone (75 ml) in place of acetone (100 ml). Reaction was largely complete after the first overnight period, addition of more OXONE $^R$ (100 g) and alkali, followed by a further overnight reaction period led to the consumption of essentially all alkene. Work up gave epoxide (6.84 g), following final trituration with ether-hexane.

EXAMPLE 52

This Example illustrates the preparation of diethyl (2RS,3RS)-2,3-epoxy-3(1-trityl-1,2,4-triazol-3-yl)propane phosphonate having the structural formula (XXIV).

A stirred solution of diethyl Z-3(1-trityl-1,2,4-triazol-3-yl)-prop-2-enephosphonate (0.063 g, prepared as described in Example 16) in acetone (20 ml) was cooled to 0° C., then treated with solution of dimethyldioxirane (23.5 ml, 0.055M in acetone). It was allowed to stand for three days at room temperature and evaporated under reduced pressure. The residue was chromatographed on silica, using ethyl acetate as eluant, to give the title compound (0.40 g) as a viscous oil. NMR (CDCl$_3$): $\delta$ 1.23(6H,t), 2.42(2H,m), 3.60(1H,m), 4.02(4H,m), 4.18(1H,d), 7.05–7.40(15H,m), 7.95(1H,s).

EXAMPLE 53

This Example illustrates the preparation of (2RS,3SR)-3-chloro-2-hydroxy-3(1,2,4-triazol-3-yl)propane phosphonic acid (Compound No. 13 in Table 1).

2M Hydrochloric acid (15 ml) was added to a stirred solution of diisopropyl(2RS,3SR)-2,3-epoxy-3(1-trityl-1,2,4-triazol-3-yl)propane phosphonate (0.40 g, prepared as described in Example 51) in tetrahydrofuran (15 ml). The mixture was allowed to stand for three days, concentrated under reduced pressure to a volume of 15 ml, then extracted with ethyl acetate (2×20 ml). The aqueous layer was freeze-dried to give crude diisopropyl (2RS,3SR)-3-chloro-2-hydroxy-3(1,2,4-triazol-3-yl)propane phosphonate (0.23 g) as a pale yellow oil, probably as its hydrochloride. 2D-NMR confirmed regiochemistry.

A stirred solution of this material in dichloromethane (5 ml) was treated with trimethylsilyl bromide (1.7 ml) and the mixture allowed to stand for two days. It was evaporated under reduced pressure and the residue azeotroped with methanol (2×25 ml), then hexane (25 ml). The crude product was retreated with trimethylsilyl bromide, worked up as above, then chromatographed on Amberlite CG-120(H+) resin, using water as eluant. Appropriate fractions were freeze-dried to give the title compound (0.044 g, m.p. shrinks 60° C., dec 150° C.). NMR (D$_2$O): $\delta$1.7–2.1(2H,m), 4.3(1H,m), 5.05(1H,d), 8.43(1H,s). (No internal standard, solvent signal at $\delta$4.62). FAB M/S: M+ 241, 243.

EXAMPLE 54

This Example illustrates the preparation of (2RS,3RS)-3-chloro-2-hydroxy-3(1,2,4-triazol-3-yl)propane phosphonic acid (Compound No. 40 in Table I).

Diethyl (2RS,3RS)-2,3-epoxy-3(1-trityl-1,2,4-triazol-3-yl)propane phosphonate (0.39 g, prepared as described in Example 52) was treated with hydrochloric acid, as described in Example 53 for the (RS,SR) isomer, to give diethyl (2RS, 3RS)-3-chloro-2-hydroxy-3(1,2,4-triazol-3-yl)propane phosphonate (0.21 g) as a colourless oil, probably as its hydrochloride. NMR(D$_2$O): $\delta$1.15(6H,t), 2.15(2H,m), 4.00(4H,m), 4.45(1H,m), 5.17(1H,d), 8.75(1H,s). (No internal standard, solvent signal at $\delta$4.67).

Silicon-mediated deesterification of the above material (0.21 g), as described for the diastereoisomer in Example 53, was again incomplete after one treatment, and required a second cycle. Chromatography on Amberlite CG-120(H+) resin, with freeze-drying of appropriate fractions, gave the title compound (0.098 g, m.p. softens 48° C., dec. 155° C.). NMR (D$_2$O): 1.83–2.08(2H,m), 4.40(1H,m), 5.27(1H,d), 8.56(1H,s). (No internal standard, solvent signal at $\delta$4.72). FAB M/S: MH+ 242,244.

EXAMPLE 55

This Example illustrates the preparation of (2RS,3RS)-3-azido-2-hydroxy-3(1,2,4-triazol-3-yl)propane phosphonic acid (Compound No. 14 in Table 1).

A mixture of diisopropyl (2RS,3SR)-2,3-epoxy-3(1-trityl-1,2,4-triazol-3-yl)propane phosphonate (6.83 g prepared as described in Example 51), sodium azide (4.18 g), ammonium chloride (1.51 g) and methanol-water (8:1, 125 ml) was heated under reflux for six hours, then concentrated under reduced pressure. The residue was filtered through silica in chloroform, then chromatographed on silica, using ethyl acetate-ethanol (20:1) as eluant, to give diisopropyl (2RS,3RS)-3-azido-2-hydroxy-3(1-trityl-1,2,4-triazol-3-yl)propane phosphonate (5.22 g, m.p. 137°–139° C., after trituration with ether). IR (nujol): 3304, 2104 cm$^{-1}$. NMR (CDCl$_3$: $\delta$1.3(12H,m), 1.9–2.25(2H,m), 4.17(1H,d), 4.45(1H,m), 4.68(2H,m), 4.78(1H,d), 7.1–7.4(15H,m), 7.98(1H,s). $^{13}$C NMR confirmed the regiochemistry.

Trimethylsilyl bromide (6.3 ml) was added to a stirred solution of this azido-ester (1.07 g) in dry dichloromethane (30 ml). The mixture was allowed to stand for eighteen hours at room temperature, evaporated under reduced pressure and the residue azeotroped under reduced pressure with methanol (2×25 ml), then hexane (25 ml). The residue was partitioned between water and ethyl acetate. The aqueous layer was freeze-dried, then chromatographed on Amberlite CG-120(H+) resin using water as eluant. Appropriate fractions were freeze-dried to give the title compound (0.40 g, m.p. 82°–85° C. dec, then 130°–135° C. with gas evolution). IR (nujol): 2114 cm$^{-1}$. NMR (D$_2$O): $\delta$1.85–2.1(2H,m), 4.4(1H,m), 5.03(1H,d), 8.7(1H,s). FAB M/S: MH+ 249.

EXAMPLE 56

This Example illustrates the preparation of (2RS,3RS)-3-amino-2-hydroxy-3(1,2,4-triazol-3-yl)propane phosphonic acid (Compound No. 15 in Table 1).

A mixture of (2RS,3RS)-3-azido-2-hydroxy-3(1,2,4-triazol-3-yl)propane phosphonic acid (0.35 g, prepared as described in Example 55), platinum oxide (17 mg) and water (25 ml) was stirred under hydrogen for three days, filtered through Hyflo Super-Cel, and freeze-dried to give the title compound (0.21 g, m.p. softens 195° C., 202°–204° C. dec). NMR (D$_2$O): $\delta$ 1.6–2.0(2H,m), 4.51(1H,m), 4.79(1H,d), 8.54(1H,s). FAB M/S: MH+ 223.

EXAMPLE 57

This Example illustrates the preparation of (2RS,3SR)-3-amino-2-hydroxy-3(1,2,4-triazol-3-yl)propane phosphonic acid (Compound No. 16 in Table 1).

A mixture of N-chloro-N-sodio-t-butylcarbamate (2.6 g, prepared as described in J. Amer. Chem. Soc., 1978, 100, 3596), silver nitrate (5.1 g) and acetonitrile (100 ml) was stirred at room temperature for fifteen minutes. To this stirred suspension was added diisopropyl E-3(1-trityl-1,2,4-triazol-3-yl)prop-2-ene phosphonate (2.6 g, prepared as described in Example 15), osmium tetroxide (2.5 ml, 2.5% w/w in t-butanol) and water (0.81 ml). The reaction mixture was stirred for seven hours, allowed to stand overnight, diluted with chloroform (100 ml) and evaporated under reduced pressure. The brown oil was extracted with chloroform and the extracts filtered through Hyflo Super-Cel, evaporated and the residue chromatographed on silica, using ethyl acetate-ethanol (25:1) as eluant.

The product was triturated with hexane to give diisopropyl (2RS,3SR)-3-t-butoxycarbonylamino-2-hydroxy-3(1-trityl-1,2,4-triazol-3-yl)propane phosphonate (0.64 g, m.p. 133°–135° C.). NMR (CDCl$_3$): $\delta$1.3(12H,m), 1.43(9H,s), 2.0(2H,dd), 4.0(1H,br), 4.45(1H,m), 4.7(2H,m), 4.93(1H,d), 5.64(1H,d), 7.1–7.4(15H,m), 7.88(1H,s). $^{13}$C-$^1$H correlation NMR confirmed the regiochemistry given.

A mixture of this material (0.58 g), trimethylsilyl bromide (3.0 ml) and dry dichloromethane (10 ml) was allowed to stand for twenty hours at room temperature. It was then evaporated under reduced pressure, azeotroped under reduced pressure with methanol (2×10 ml) and then hexane (10 ml). The residue was partitioned between chloroform (20 ml) and water (10 ml). The aqueous layer was freeze-dried and the residue chromatographed on Amberlite CG-120(H+) resin, using water, then 0.5N ammonium hydroxide, as eluants. Appropriate fractions were freeze-dried to give the title compound (0.16 g, m.p. 108°–110° C. dec). NMR (D$_2$O): $\delta$1.53(2H,dd), 4.20(1H,m), 4.28(1H,d), 8.25(1H,s). (No internal standard, solvent signal at $\delta$4.70). $^{13}$C NMR was used to confirm the structure given. FAB M/S: MH+ 223.

EXAMPLE 58

This Example illustrates the preparation of diisopropyl (2RS,3RS)-2,3-epimino-3(1-trityl-1,2,4-triazol-3-yl)propane phosphonate having the structural formula (XXII).

A mixture of diisopropyl (2RS,3RS)-3-azido-2-hydroxy-3(1-trityl-1,2,4-triazol-3-yl)propane phosphonate (4.39 g, prepared as described in Example 55), triphenylphosphine (2.0 g), triphenylphosphine hydrobromide (0.13 g) and dry tetrahydrofuran (75 ml) was stirred at room temperature under nitrogen for ninety minutes, then heated under reflux for a further four hours. It was then evaporated under reduced pressure, the residue extracted with ether, and the supernatants evaporated under reduced pressure. This residue was chromatographed on silica, using chloroform-hexane-methanol (15:3:1) as eluant to give the title compound (3.43 g, m.p. 145°–147° C.). NMR (CDCl$_3$): $\delta$1.28(12H,t), 1.8–2.15(2H,m), 2.68(1H,m), 2.93(1H,d), 4.7(2H,m), 7.1–7.4(15H,m), 7.84(1H,s).

EXAMPLE 59

This Example illustrates the preparation of (2RS,3SR)-2-amino-3-azido- 3(1,2,4-triazol-3-yl)propane phosphonic acid (Compound No. 17 in Table 1).

A stirred mixture of diisopropyl(2RS,3RS)-2,3-epimino-3(1-trityl-1,2,4-triazol-3-yl)propane phosphonate (2.6 g, prepared as described in Example 58), sodium azide (1.59 g), ammonium chloride (0.58 g) and methanol-water (8:1, 50 ml) was heated under reflux for six hours, then allowed to stand at room temperature for three days. Further quantities of sodium azide (0.80 g) and ammonium chloride (0.29 g) were added and the mixture heated for a further six hours. It was then filtered through silica, using chloroform as eluant, dried, evaporated and chromatographed on silica, using chloroform-hexane-methanol (15:3:1) as eluant, to give diisopropyl(2RS,3SR)-2-amino-3-azido-3(1-trityl-1,2,4-triazol-3-yl)propane phosphonate (2.27 g) as a yellow oil. NMR (CDCl$_3$): $\delta$1.3(12H,m), 1.65–1.85(1H,m), 2.12–2.28(1H,m), 3.65(1H,m), 4.58(1H,d), 4.68(2H,m), 7.05–7.38(15H,m), 8.00(1H,s). Regiochemistry was confirmed by extensive NMR studies on acetylated material.

A mixture of the above azidoamine (1.84 g), trimethylsilyl bromide (10.6 ml) and dry dichloromethane (25 ml) was allowed to stand for twenty hours at room temperature, evaporated under reduced pressure and azeotroped under reduced pressure with methanol (2×25 ml), then hexane (25 ml). The residue was partitioned between water and ethyl acetate and the aqueous layer evaporated under reduced pressure. The oil obtained was chromatographed on Amberlite CG-120(H+) resin to give, after freeze-drying, the title compound as a pale yellow hygroscopic solid (0.37 g). NMR (D$_2$O): $\delta$1.66–1.90(2H,m), 3.85(1H,m), 5.28(1H,d), 8.48(1H,s). (No internal standard, solvent signal at $\delta$4.69). FAB M/S: MH+ 248.

EXAMPLE 60

This Example illustrates the preparation of (2RS,3SR)-2,3-diamino-3-(1,2,4-triazol-3-yl)propane phosphonic acid (Compound No. 18 in Table 1).

A mixture of (2RS,3SR)-2-amino-3-azido-3(1,2,4-triazol-3-yl)propane phosphonic acid (0.205 g, prepared as described in Example 59), platinum oxide (0.010 g) and water (15 ml) was stirred under hydrogen for twenty hours. It was filtered through Hyflo Super-Cel and freeze-dried to give the title compound (0.165 mg, m.p. 198°–200° C., dec). NMR (D$_2$O): $\delta$1.78–2.15(2H,m), 4.08(1H,m), 4.88(1H,d), 8.52(1H,s). (No internal standard, solvent signal at $\delta$4.76). FAB M/S: MH+ 222.

EXAMPLE 61

This Example illustrates the preparation of (2RS,3SR; 2RS,3RS)-2-amino-3-hydroxy-3(1,2,4-triazol-3-yl)propane phosphonic acid, as a mixture of diastereoisomers. (Compounds No. 19 and 20 in Table 1).

2-(tert-Butoxycarbonyloxyimino)-2-phenylacetonitrile (BOC-ON, 2.82 g) was added portionwise to a stirred solution of diisopropyl (2RS,3RS)-2,3-epimino-3(1-trityl-1,2,4-triazol-3-yl)propane phosphonate (2.76 g, prepared as described in Example 58) and triethylamine (2.17 ml) in dioxan-water (2:1, 75 ml). The mixture was stirred at room temperature for seven hours, allowed to stand for a further three days, diluted with water (50 ml) and extracted with chloroform (3×50 ml). The organic layers were dried over magnesium sulphate and evaporated under reduced pressure. The residue was purified using HPLC on silica, with ethyl acetate as eluant, to give diisopropyl (2RS,3RS)-2,3(N-tert-butoxycarbonylepimino-3(1-trityl-1,2,4-triazol-3-yl)propane phosphonate (1.22 g, m.p. 30°–31° C.). NMR (CDCl$_3$): $\delta$ 1.25(12H,m), 1.33(9H,s), 1.70(1H,m), 2.23(1H,m), 3.35(1H,m), 3.53(1H,d), 4.68(2H,m), 7.1–7.4(15H,m), 7.85(1H,s). IR: 1724 cm$^{-1}$.

A stirred solution of this material (2.30 g) in dry dichloromethane (50 ml) was treated with trimethylsilyl bromide (12 ml). The mixture was allowed to stand for three days at room temperature, evaporated under reduced pressure, and the residue partitioned between water (50 ml) and chloroform (50 ml). The aqueous layer was filtered through Hyflo Super-Cel, evaporated under reduced pressure and the residue chromatographed on Amberlite CG-120(H+) resin, using water then 0.5N ammonium hydroxide solution as eluants, to give after freeze-drying the title compound (0.25 g, m.p. 250° C. dec) as a 1:1 mixture of diastereoisomers, regiochemically pure but contaminated with a third component. NMR (D$_2$O): 1.3–2.3(2H,m), 3.7(0.5H,m), 3.85(0.5H,m), 4.87(0.5H,d), 5.0(0.5H,d), 8.27(0.5H,s), 8.32(0.5H,s). FAB M/S: MH+ 223.

Further purification on acid resin removed the impurity but also caused epimerization giving a 9:1 mixture of diastereoisomers, (m.p. 78°–81° C. dec). It was this material which was used for biological testing. Comparison of the NMR spectra of the sodium salts of this mixture with those of the salts of the separate diols (Compound No. 10 and 12 of Table I) suggested that the major diastereoisomer had the 2RS,3SR configuration.

EXAMPLE 62

This Example illustrates the preparation of the sodium salt of 2-hydroxy-5(1,2,4-triazol-3-yl)-1,2-oxaphospholane 2-oxide (Compound No. 41 in Table I).

3(1,2,4-Triazol-3-yl)propane phosphonic acids having an additional leaving group, for example halogen or nitrosyloxy, at the 3-position cyclize when the pH is raised to give salts of the lactol derived from 3-hydroxy-3(1,2,4-triazol-3-yl)propane phosphonic acid, alternatively named as shown in the title.

Thus 3-chloro-3(1,2,4-triazol-3-yl)propane phosphonic acid (0.072 g, prepared as described in Example 28) was dissolved in a solution of disodium hydrogen phosphate (0.18 g) in water (2.0 ml). $^{31}$P NMR showed an almost immediate conversion into the title compound; 43.5 ppm downfield from phosphate buffer standard versus 23 ppm for the sodium salt of uncyclized 3-hydroxyphosphonate.

Cyclization of the diastereoisomeric chlorohydrins, prepared as described in Examples 53 and 54, in a similar manner proceeds with inversion of configuration at C-3. Thus the 2RS,3SR isomer gives the sodium salt of (4RS,5SR)-2,4-hydroxy-5(1,2,4-triazol-3-yl)-1,2-oxaphospholane 2-oxide whereas the 2RS,3RS isomer gives the 4RS,5RS product. Appropriate low-field phosphorus resonances are observed.

EXAMPLE 63

This Example illustrates the preparation of 2-(1,2,4-triazol-3-yl)cyclopropane phosphonic acid, probably having the 1RS,2RS configuration (Compound No. 42 in Table I).

Lithium diisopropylamide (0.91 ml, 1.5M in cyclohexane) was added dropwise under nitrogen to a stirred solution of diethyl 3-fluoro-3(1-trityl-1,2,4-triazol-3-yl)propane phosphonate (0.35 g, prepared as described in Example 27) whilst maintaining the temperature below −60° C. After five hours, the mixture was allowed to warm then stand at room temperature overnight. It was then poured on to saturated ammonium chloride solution and extracted with ethyl acetate. The extracts were dried over magnesium sulphate and evaporated under reduced pressure. The residue was chromatographed on silica, using dichloromethane-ethanol (19:1) as eluant, to give diethyl 2(1-trityl-1,2,4-triazol-3-yl)cyclopropane phosphonate (0.18 g). NMR (CDCl$_3$): δ1.3(6H,2xt), 1.4–1.5(3H,m), 2.6–2.7(1H,m), 4.05–4.2(4H,m), 7.1–7.3(15H,m), 7.8(1H,s). M/S: M+ 487. The basic structure was confirmed by $^{13}$C, $^{19}$F, $^{31}$P, COSY and NOESY experiments but stereochemistry could not be assigned. Theoretical calculations suggested that the trans (1RS,2RS) isomer is likely to be much more stable and thus preferred.

This material (0.10 g) was deprotected as described in Example 39 to give the title compound as a white gum (0.034 g). NMR (D$_2$O): δ1.3–1.5(3H,m), 2.3–2.4(1H,m), 8.7(1H,s). FAB M/S: MH+ 190.

EXAMPLE 64

This Example illustrates the preparation of 3(bromoacetoxy)-3(1,2,4-triazol-3-yl)propane phosphonic acid (Compound No. 43 in Table I).

Diethyl 3-hydroxy-3(1-trityl-1,2,4-triazol-3-yl)propane phosphonate (1.0 g, prepared as described in Example 24) was acylated with bromoacetyl bromide (0.50 g) in a manner similar to the acetylation described in Example 26. Diethyl 3(bromoacetoxy)-3(1-trityl-1,2,4-triazol-3-yl)propane phosphonate (0.40 g) was isolated as a colourless gum. NMR (CDCl$_3$): δ 1.3(6H,t), 1.7–1.9(2H,m), 2.3(2H,m), 3.8–3.95(2H,m), 4.1(4H,m), 6.0(1H,t), 7.1–7.3(15H,m), 7.9(1H,2xs). FAB M/S: MH+ 626,628. IR: 1746 cm$^{-1}$, carbonyl.

Deprotection of this material (0.40 g), similar to that described in Example 26, gave a mixture (0.089 g, m.p. 88°–93° C.) of the title compound and 3-hydroxy-3(1,2,4-triazol-3-yl)propane phosphonic acid in a ratio of 11:9. NMR (D$_2$O) of bromoacetate only: δ1.4–1.6(2H,m), 1.9–2.2(2H,m), 3.95(2H,m), 5.8(1H,t), 8.4(1H,s).

EXAMPLE 65

This Example illustrates the preparation of 3-hydroxy-3-trifluoromethyl-3(1,2,4-triazol-3-yl)propane phosphonic acid (Compound No. 44 in Table I).

(Trifluoromethyl)trimethylsilane (0.35 g), then tetrabutylammonium fluoride (0.05 ml, 1M solution in tetrahydrofuran), were added to a stirred and ice-cooled solution of diethyl 3-oxo-3(1-trityl-1,2,4-triazol-3-yl)propane phosphonate (1.0 g, prepared as described in Example 42) in dry tetrahydrofuran (15 ml). The mixture was allowed to warm to room temperature, to stand overnight, then poured into water and extracted with ethyl acetate. The extracts were washed with brine, dried over magnesium sulphate and evaporated under reduced pressure to give diethyl 3-trifluoromethyl-3-trimethylsilyloxy-3(1-trityl-1,2,4-triazol-3-yl)propane phosphonate (1.2 g) as a yellow oil. NMR (CDCl$_3$): δ0.00(9H,s), 1.3(6H,m), 1.7–1.95(2H,m), 2.2–2.5(2H,m), 3.9–4.2 (4H,m), 7.1–7.3(15H,m), 8.0(1H,s). M/S: M+ 645.

A solution of this material in dichloromethane was treated with trimethylsilyl bromide as described in Example 24 to give, after ion-exchange chromatography, the title compound. NMR (D$_2$O): δ1.1–1.3(1H,m), 1.6–1.8(1H,m), 2.2–2.5(2H,m), 8.45(1H,s). FAB M/S: MH+ 276.

EXAMPLE 66

This Example illustrates the preparation of (1RS,3RS; 1RS,3SR)-1-fluoro-3-hydroxy-3(1,2,4-triazol-3-yl)propane phosphonic acids (Compound No. 45 in Table 1) and also the corresponding O-methyl ethers (Compound No. 46 in Table 1).

A solution of lithium diisopropylamide (1.75 ml, 1.5M in cyclohexane) was added dropwise, with stirring, to a solution of diethyl 3-methoxy-3(1-trityl-1,2,4-triazol-3-yl)propane phosphonate (0.65 g, prepared as described in Example 25) in dry tetrahydrofuran (15 ml), under nitrogen and with temperature maintained below −60°

C. After a further twenty minutes, a solution of N-fluorobenzenesulphonimide (0.51 g) in tetrahydrofuran (15 ml) was added dropwise to the stirred reaction mixture at below −60° C. The mixture was stirred for a further two hours at −78° C., allowed to warm to room temperature and to stand overnight. It was then poured into saturated ammonium chloride solution and extracted with ethyl acetate. The extracts were washed with brine, dried over magnesium sulphate and evaporated under reduced pressure. The residue was chromatographed on silica, using dichloromethane-ethanol (49:1) as eluant, to give diethyl (1RS,3RS; 1RS,3SR)-1-fluoro-3-methoxy-3(1-trityl-1,2,4--triazol-3-yl)propane phosphonate (0.21 g) as an oily mixture of diastereoisomers in a ratio of 3:1 or 1:3. NMR (CDCl$_3$): $\delta$1.3(6H,2t), 2.5–2.7(2H,m), 3.3(3H,2xs), 4.2(4H,m), 4.6–4.8(2H,m), 7.1–7.3(15H,m), 8.0(1H,2xs). M/S: M+ 537. The structures were confirmed by $^{19}$F and $^{13}$C NMR.

A solution of this material in dichloromethane was treated with trimethylsilyl bromide as described in Example 24 to give, after ion-exchange chromatography, 1-fluoro-3-methoxy-3(1,2,4-triazol-3-yl) propane phosphonic acid (Compound No. 46 in Table 1) also as a mixture of diastereoisomers in a ratio of 3:1 or 1:3. NMR(D$_2$O): $\delta$2.15–2.4(2H,m); 3.25(3H,s); 4.4–4.8(1H,m); 4.85(1H,t); 8.9(1H,2xs). FAB M/S: MH+ 240. More vigorous deprotection, for example in the presence of iodide ion, will result in ether cleavage to give 1-fluoro-3-hydroxy-3(1,2,4-triazol-3-yl)propane phosphonic acid (Compound No. 45 in Table 1), also as a mixture of diastereoisomers. Biological Data The herbicidal activity of the compounds was tested as follows:

Each chemical was formulated in one of two ways. Either the chemical was dissolved in an appropriate amount of water, dependent on the amount of solvent-/surfactant blend required such that the total volume is 5 cm$^3$. Then a solvent sufficient blend comprised 78.2 gm/liter of Tween 20 and 21.8 gm/liter of Span 80 adjusted to 1 liter using methylcyclohexanone was added to the solution. Alternatively, the chemical was dissolved in water to the required concentration and 0.1% Tween added. Tween 20 is a Trade Mark for a surface-active agent comprising a condensate of 20 molar proportions of ethylene oxide with sorbitan laurate. Span 80 is a Trade Mark for a surface-active agent comprising sorbitan mono-laurate. If the chemical did not dissolve, the volume was made up to 5 cm$^3$ with water, glass beads were added and this mixture was then shaken to effect dissolution or suspension of the chemical, after which the beads were removed. In all cases, the mixture was then diluted to the required spray volume. If sprayed independently, volumes of 25 cm$^3$ and 30 cm$^3$ were required for post-emergence tests; if sprayed together, 45 cm$^3$ was required. The sprayed aqueous emulsion contained 4% of the initial solvent-/surfactant mix and the test chemical at an appropriate concentration.

The spray compositions so prepared were sprayed on to young pot plants (post-emergence test) at a spray volume equivalent to 1000 liters per hectare. Damage to plants was assessed 13 days after spraying by comparison with untreated plants, on a scale of 0 to 9 where 0 is 0% damage, 1 is 1–5% damage, 2 is 6–15% damage, 3 is 16–25% damage, 4 is 26–35% damage, 5 is 36–59% damage, 6 is 60–69% damage, 7 is 70–79% damage, 8 is 80–89% damage and 9 is 90–100% damage.

The results of the tests are given in Table II below.

TABLE II

| COMPOUND NO. | RATE OF APPLN kg/ha | BV | BN | GH | GM | ZM | OS | TA | PA | CA | GA | AR | BP | EH | IH | AT | XT | AF | AM | AE | SH | SV | DS | EC | CR | CE |
|---|---|---|---|---|---|---|---|---|---|---|---|---|---|---|---|---|---|---|---|---|---|---|---|---|---|---|
| 4 | 1 | 3 | — | — | 2 | 5 | 4 | — | 7 | 4 | 0 | 3 | — | 2 | 0 | 3 | 0 | 6 | 5 | — | 5 | 7 | — | 8 | — | 5 |
| 5 | 1 | 0 | 7 | — | 3 | 5 | 5 | 6 | 2 | 6 | 3 | 0 | — | 3 | 2 | 8 | 0 | 5 | 5 | — | 6 | 8 | — | 5 | — | 0 |
| 6 | 2 | 4 | 0 | — | 0 | 0 | 5 | 0 | 0 | 0 | 6 | 3 | 3 | 0 | 0 | 2 | — | 0 | 0 | 3 | 6 | 0 | 6 | 0 | — | 5 |
| 7 | 2 | 6 | 0 | — | 4 | 3 | 4 | 4 | 8 | 3 | 0 | 0 | — | 0 | 6 | 3 | 9 | 4 | 0 | — | 0 | 3 | — | 3 | — | 7 |
| 8 | 1 | 6 | 4 | — | 5 | 6 | 7 | 8 | 6 | 8 | 7 | 9 | — | 8 | 8 | 4 | 0 | 8 | 8 | — | 9 | 9 | — | 9 | — | — |
| 9 | 2 | 6 | 6 | — | 6 | 6 | 4 | 4 | 0 | 6 | 6 | 8 | 4 | — | — | 6 | 0 | 2 | 4 | 4 | 6 | 6 | 6 | 6 | 0 | — |
| 10 | 1 | 5 | 0 | 4 | 0 | 6 | 6 | 5 | 0 | 5 | 5 | 9 | 2 | 5 | 4 | 0 | 0 | 5 | 5 | 7 | 8 | 7 | 8 | 9 | 5 | 1 |
| 12 | 2 | — | — | 4 | — | 3 | 3 | 5 | 4 | 0 | 3 | 0 | 0 | 0 | 0 | 2 | — | — | 0 | 0 | 0 | 7 | 0 | — | — | 8 |
| 15 | 2 | 6 | 2 | — | 3 | 9 | 4 | 8 | 9 | 3 | 2 | 4 | 7 | 7 | 5 | — | 0 | 7 | 4 | 8 | 9 | 9 | 9 | 1 | — | 8 |
| 16 | 2 | 4 | 4 | — | 3 | 8 | 2 | 5 | 9 | 5 | 6 | 6 | 5 | 7 | 9 | 0 | 3 | 9 | 9 | 7 | 9 | 9 | 8 | 8 | — | 5 |
| 18 | 2 | 6 | 4 | — | 3 | 8 | 0 | 5 | 0 | 4 | 8 | 7 | 5 | 7 | 2 | 1 | 3 | 2 | 4 | 3 | 8 | 8 | 9 | 5 | — | 0 |
| 23 | 1 | 0 | 3 | — | 0 | 0 | 2 | 5 | 0 | 4 | 8 | 0 | 0 | 0 | 0 | 2 | 6 | 1 | 2 | 0 | 0 | 5 | — | 3 | — | 0 |
| 24 | 1 | 0 | 0 | — | 0 | 0 | 0 | 5 | 5 | 7 | 0 | 6 | — | 4 | 0 | 0 | 0 | 8 | 0 | — | 0 | 0 | — | 0 | — | 0 |
| 25 | 1 | 5 | 8 | — | 2 | 7 | 2 | 7 | 7 | 6 | 0 | 7 | — | 3 | 7 | 5 | 0 | 7 | 8 | — | 9 | 9 | — | 8 | — | 7 |
| 26 | 1 | 4 | 7 | — | 7 | 6 | 7 | 8 | 8 | 8 | 7 | 9 | — | 6 | 5 | 5 | 3 | 6 | 8 | — | 9 | — | — | 9 | — | 5 |
| 27 | 1 | 5 | 5 | — | 5 | 8 | 6 | 6 | 8 | 2 | 6 | 7 | — | 5 | 7 | 7 | 6 | 8 | 8 | — | 9 | 8 | — | 8 | — | 7 |
| 28 | 1 | 2 | 0 | — | 0 | 0 | 5 | 8 | 2 | 8 | 2 | 9 | — | — | — | 0 | 3 | 8 | 0 | — | 0 | 0 | — | 9 | — | 2 |
| 29 | 1 | 2 | 2 | — | — | 0 | 0 | 6 | 0 | 0 | 0 | 0 | — | — | — | 0 | 0 | 1 | 0 | — | — | 5 | — | 7 | — | 0 |
| 30 | 1 | 2 | 6 | — | — | 7 | 6 | 2 | 8 | 3 | 3 | 0 | — | 6 | — | 7 | 0 | 0 | 8 | — | 1 | 8 | — | 0 | — | 0 |
| 31 | 1 | 2 | 2 | — | 5 | 2 | 2 | 6 | 2 | 6 | 5 | 0 | — | — | 1 | 0 | — | 2 | 1 | — | 0 | 0 | — | 2 | — | 6 |
| 32 | 1 | 6 | 0 | — | 0 | 5 | 1 | 2 | 0 | 2 | 0 | 8 | — | 2 | 2 | 2 | 0 | 2 | 2 | — | 3 | 5 | — | 8 | — | 9 |
| 33 | 1 | 0 | 0 | — | 2 | 0 | 1 | 1 | 0 | 0 | 3 | 0 | — | 5 | 0 | 0 | 1 | 0 | 0 | — | 0 | 0 | — | 2 | — | 2 |
| 34 | 1 | 0 | 4 | — | 3 | 0 | 3 | 0 | 3 | 0 | 0 | 1 | — | 4 | 3 | 3 | 0 | 0 | 0 | — | 0 | 8 | — | 0 | — | 0 |
| 35 | 0.942 | 0 | 0 | — | 0 | 0 | 0 | 0 | 0 | 0 | 0 | 0 | — | 0 | 0 | 0 | 0 | 0 | 0 | — | 0 | 5 | — | 0 | — | 0 |
| 36 | 1 | 0 | 0 | — | 0 | 0 | 0 | 0 | 0 | 0 | 2 | 2 | — | 0 | 0 | 0 | 0 | 0 | 0 | — | 0 | 8 | — | 2 | — | 0 |
| 37 | 1 | 2 | 4 | — | 0 | 6 | 7 | 8 | 2 | 8 | 0 | 0 | — | 8 | 8 | 4 | 2 | 8 | 1 | — | 0 | 0 | — | 0 | — | 4 |
| 38 | 0.914 | 6 | 0 | — | 5 | 6 | 5 | 7 | 8 | 8 | 7 | 9 | — | 0 | 0 | — | 0 | 0 | 8 | — | 0 | 5 | — | 2 | — | 2 |
| 39 | 1 | 6 | 4 | — | 3 | 3 | 8 | 7 | 2 | 3 | 5 | 5 | — | 8 | 8 | 1 | 2 | 8 | 2 | — | 1 | 9 | — | 9 | — | 7 |
| 40 | 1 | 3 | — | — | 3 | 8 | 8 | 6 | 8 | 9 | 8 | 8 | — | 0 | 0 | 9 | 7 | 7 | 8 | — | 2 | 5 | — | 9 | — | 7 |
| 41 | 1.122 | 6 | 6 | — | 3 | 8 | 5 | 3 | 7 | 3 | 8 | 8 | — | 5 | 8 | 0 | 7 | 7 | 0 | — | 6 | 9 | — | 8 | — | 8 |
| 42 | 0.943 | 0 | 0 | — | 1 | 3 | 5 | 3 | 3 | 3 | 2 | 0 | — | 0 | 0 | 0 | 0 | 0 | 0 | — | 0 | 7 | — | 3 | — | 0 |

TABLE III
Abbreviations used for Test Plants

BV - Sugar beet
BN - Rape
GH - Cotton
GM - Soybean
ZM - Maize
OS - Rice
TA - Winter wheat
PA - *Polygonum aviculare*
CA - *Chenopodium album*
GA - *Galium aparine*
AR - *Amaranthus retroflexus*
BP - *Bidens pilosa*
EH - *Euphorbia heterophylla*
IH - *Ipomoea hederacea* (post-emergence)
IX - *Ipomoea hederacea* spp hed/int
AT - *Abutilon theophrasti*
XT - *Xanthium strumarium*
AF - *Avena fatua*
AM - *Alopecurus myosuroides*
AE - *Agropyron repens*
SH - *Sorghum halepense*
SV - *Setaria viridis*
DS - *Digitaria sanguinalis*
EC - *Echinochloa crus-galli*
CR - *Cyperus rotundus*
CE - *Cyperus esculentus*

TABLE 1

| Compound No. | Structure |
|---|---|
| 1 | (triazole)-CH₂CH₂CH₂-P(O)(OH)₂ |
| 2 | (triazole)-CH=CH-CH₂-P(O)(OH)₂ |
| 3 | (triazole)-CH=CH-CHF-P(O)(OH)₂ |
| 4 | (triazole)-CH(OH)-CH₂CH₂-P(O)(OH)₂ |
| 5 | (triazole)-CHF-CH₂CH₂-P(O)(OH)₂ |
| 6 | (triazole)-C(=O)-CH₂CH₂-P(O)(OH)₂ |
| 7 | (triazole)-C(=NOH)-CH₂CH₂-P(O)(OH)₂ |
| 8 | (triazole)-C(NH₂)-CH₂CH₂-P(O)(OH)₂ |
| 9 | (triazole)-CH₂-CH(OH)-CH₂-P(O)(OH)₂ |
| 10 | (triazole)-CH(OH)-CH(OH)-CH₂-P(O)(OH)₂ |
| 11 | (triazole)-CH(-O-)CH-CH₂-P(O)(OH)₂ (epoxide) |
| 12 | (triazole)-CH(OH)-CH(OH)-CH₂-P(O)(OH)₂ |
| 13 | (triazole)-CH(Cl)-CH(OH)-CH₂-P(O)(OH)₂ |

TABLE 1-continued

| Compound No. | Structure |
|---|---|
| 14 | (triazole)-CH(N₃)-CH(OH)-CH₂-P(O)(OH)₂ |
| 15 | (triazole)-CH(NH₂)-CH(OH)-CH₂-P(O)(OH)₂ |
| 16 | (triazole)-CH(NH₂)-CH(OH)-CH₂-P(O)(OH)₂ |
| 17 | (triazole)-CH(N₃)-CH(NH₂)-CH₂-P(O)(OH)₂ |
| 18 | (triazole)-CH(NH₂)-CH(NH₂)-CH₂-P(O)(OH)₂ |
| 19 | (triazole)-CH(OH)-CH(NH₂)-CH₂-P(O)(OH)₂ |
| 20 | (triazole)-CH(OH)-CH(NH₂)-CH₂-P(O)(OH)₂ |
| 21 | (triazole)-CH₂-CH₂-CHF-P(O)(OH)₂ |
| 22 | (triazole)-CH(OH)-CH(OH)-CHF-P(O)(OH)₂ |
| 23 | (triazole)-CH(OCH₃)-CH₂-CH₂-P(O)(OH)₂ |
| 24 | (triazole)-CH(OCOCH₃)-CH₂-CH₂-P(O)(OH)₂ |
| 25 | (triazole)-CH(Cl)-CH₂-CH₂-P(O)(OH)₂ |
| 26 | (triazole)-CH(Br)-CH₂-CH₂-P(O)(OH)₂ |
| 27 | (triazole)-CH(I)-CH₂-CH₂-P(O)(OH)₂ |
| 28 | (triazole)-CH(N₃)-CH₂-CH₂-P(O)(OH)₂ |
| 29 | (triazole)-CH(triazolyl)-CH₂-CH₂-P(O)(OH)₂ |

TABLE 1-continued

| Compound No. | Structure |
|---|---|
| 30 | 3-(1H-1,2,4-triazol-3-yl)-3-cyano-propylphosphonic acid |
| 31 | 3-(1H-1,2,4-triazol-3-yl)-3-(nitrosooxy)-propylphosphonic acid |
| 32 | 3-(1H-1,2,4-triazol-3-yl)-3-(aminooxy)-propylphosphonic acid |
| 33 | 3-(1H-1,2,4-triazol-3-yl)-3-(ethoxythiocarbonylthio)-propylphosphonic acid |
| 34 | 3-(1H-1,2,4-triazol-3-yl)-3-(acetylthio)-propylphosphonic acid |
| 35 | 3-(1H-1,2,4-triazol-3-yl)-3-mercapto-propylphosphonic acid |
| 36 | 3-(1H-1,2,4-triazol-3-yl)-3-(methylthio)-propylphosphonic acid |
| 37 | 3-(1H-1,2,4-triazol-3-yl)-3-(methylsulfinyl)-propylphosphonic acid |

TABLE 1-continued

| Compound No. | Structure |
|---|---|
| 38 | 3-(1H-1,2,4-triazol-3-yl)-3-(methylsulfonyl)-propylphosphonic acid |
| 39 | 3-(1H-1,2,4-triazol-3-yl)-3,3-difluoro-propylphosphonic acid |
| 40 | 3-(1H-1,2,4-triazol-3-yl)-3-chloro-2-hydroxy-propylphosphonic acid |
| 41 | cyclic sodium salt |
| 42 | 2-(1H-1,2,4-triazol-3-yl)-cyclopropylphosphonic acid |
| 43 | 3-(1H-1,2,4-triazol-3-yl)-3-(bromoacetoxy)-propylphosphonic acid |
| 44 | 3-(1H-1,2,4-triazol-3-yl)-3-hydroxy-3-trifluoromethyl-propylphosphonic acid |
| 45 | 3-(1H-1,2,4-triazol-3-yl)-3-hydroxy-1-fluoro-propylphosphonic acid |

TABLE 1-continued

| Compound No. | Structure |
|---|---|
| 46 | [1,2,4-triazol-3-yl-CH(OCH₃)-CH₂-CHF-P(O)(OH)₂, with NH on triazole] |

CHEMICAL FORMULAE
(in description)

$$\text{triazole-A-P(O)(OR}^1\text{)(OR}^2\text{)} \quad (I)$$

$$-\underset{R^9}{\overset{R^8}{C}}-\underset{R^{11}}{\overset{R^{10}}{C}}-\underset{R^{13}}{\overset{R^{12}}{C}}- \quad (i)$$

$$-\underset{R^9}{\overset{R^8}{C}}-\overset{R^{10a}}{C}=CH- \quad (ii)$$

$$-CH=\overset{R^{10a}}{C}-\underset{R^{13}}{\overset{R^{12}}{C}}- \quad (iii)$$

$$-C\equiv C-\underset{R^{13}}{\overset{R^{12}}{C}}- \quad (iv)$$

$$-\underset{R^9}{\overset{R^8}{C}}-C\equiv C- \quad (v)$$

$$-CH=C=CH- \quad (vi)$$

$$[\text{triazole-O-P(O)(O}^-\text{)-C(R}^9\text{)(R}^{10}\text{)-C(R}^{11}\text{)(R}^{12}\text{)(R}^{13}\text{)}]_n \, Z^{n+} \quad (IA)$$

$$B-A-P(O)(OR^{20})(OR^{21}) \quad (II)$$

$$B-A'-P(O)(OR^{20'})(OR^{21'}) \quad (IIA)$$

$$\underset{R^{22}}{\text{pyrazole}} \quad (a)$$

$$\underset{R^{22}}{\text{pyrazole}} \quad (b)$$

$$B-A'-X \quad (III)$$

$$R^{23}-P(O)(OR^{20})(OR^{21}) \quad (IV)$$

$$B-A'-OH \quad (V)$$

$$B-CH=CH-CHO \quad (VI)$$

$$B-CHO \quad (VII)$$

$$B-R^{25} \quad (VIII)$$

$$HC\equiv C-P(O)(OR^{20})(OR^{21}) \quad (IX)$$

$$H-C(O)-CH_2CH_2-P(O)(OR^{20})(OR^{21}) \quad (X)$$

$$R^{27}-C\equiv C-P(O)(OR^{20})(OR^{21}) \quad (XI)$$

$$R^{27}-C\equiv CH \quad (XII)$$

$$R^{28}P(OR^{20})(OR^{21}) \quad (XIII)$$

$$B-\underset{H}{\overset{OH}{C}}-C\equiv CH \quad (XIV)$$

INTERMEDIATES

[Triazole-N(CPh₃), with CH=CH-CH₂-P(O)(OCH(CH₃)₂)₂] (XV)

[Triazole-N(CPh₃), with CH=CH-CH₂-P(O)(OCH(CH₃)₂)₂] (XVI)

[Triazole-N(CPh₃), with C≡C-CH₂-P(O)(OCH₂CH₃)₂] (XVII)

-continued
CHEMICAL FORMULAE
(in description)

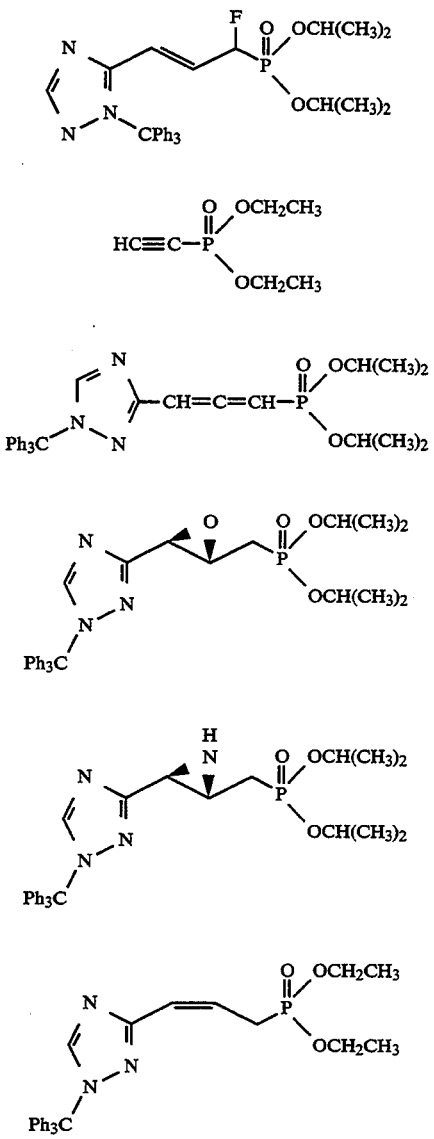

(XVIII)

(XIX)

(XX)

(XXI)

(XXII)

(XXIII)

-continued
CHEMICAL FORMULAE
(in description)

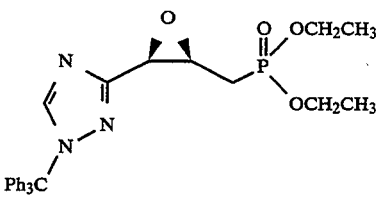

(XXIV)

What is claimed is:

1. An herbicidal compound of the formula:

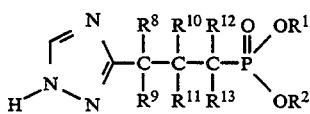

or a salt, tautomer or cyclic derivative thereof, wherein:
$R^1$ and $R^2$ are hydrogen;
$R^8$ is fluorine, chlorine, bromine, iodine, 1,2,4-triazol-1-yl, cyano, nitrosyloxy, aminoxy, amino, azido, $SCSOCH_2CH_3$, $SCOCH_3$, mercapto, methylthio, methanesulphonyl or methanesulphinyl;
$R^9$ is hydrogen or fluorine;
or $R^9$ together with $R^8$ forms an oximino group;
$R^{10}$ is hydrogen, hydroxy or amino;
or $R^9$ and $R^{10}$ together form —O—;
$R^{11}$ is hydrogen; and
$R^{12}$ and $R^{13}$ are each independently hydrogen, hydroxy or fluorine, with the proviso that when one of $R^{12}$ and $R^{13}$ is hydroxy, the other is hydrogen.

2. An herbicidal composition comprising an herbicidally effective amount of a compound according to claim 1 in combination with an herbicidal carrier or diluent.

3. A process for severely damaging or killing unwanted plants which process comprises applying to the plants, or to the growth medium of the plants, a herbicidally effective amount of a compound as defined in claim 1.

4. A compound according to claim 1 wherein $R^8$ is amino, nitrosyloxy, fluorine, chlorine, bromine or iodine.

5. A compound according to claim 4 wherein such compound is 3-amino-3-(1,2,4-triazol-3-yl)propane phosphonic acid.

* * * * *